US011532241B1

(12) United States Patent
Beaubien et al.

(10) Patent No.: US 11,532,241 B1
(45) Date of Patent: Dec. 20, 2022

(54) SIMULATION BASED TRAINING SYSTEM FOR MEASUREMENT OF COGNITIVE LOAD TO AUTOMATICALLY CUSTOMIZE SIMULATION CONTENT

(71) Applicant: Aptima, Inc., Woburn, MA (US)

(72) Inventors: Jeffrey Beaubien, Londonderry, NH (US); John Feeney, Beavercreek, OH (US); William N. DePriest, Dayton, OH (US); Scott Pappada, Waterville, OH (US)

(73) Assignee: Aptima, Inc., Woburn, MA (US)

( * ) Notice: Subject to any disclaimer, the term of this patent is extended or adjusted under 35 U.S.C. 154(b) by 0 days.

(21) Appl. No.: 17/024,325

(22) Filed: Sep. 17, 2020

Related U.S. Application Data

(63) Continuation of application No. 15/850,998, filed on Dec. 21, 2017, now Pat. No. 10,783,801.
(Continued)

(51) Int. Cl.
*A61B 5/16* (2006.01)
*G09B 9/00* (2006.01)
(Continued)

(52) U.S. Cl.
CPC ............... *G09B 9/00* (2013.01); *A61B 5/0245* (2013.01); *A61B 5/16* (2013.01); *A61B 5/369* (2021.01); *G09B 7/10* (2013.01); *G09B 19/00* (2013.01)

(58) Field of Classification Search
CPC .................................................. A61B 5/0006
See application file for complete search history.

(56) References Cited

U.S. PATENT DOCUMENTS 5,103,496 A 4/1992 Andres et al.
5,633,954 A 9/1997 Gupta et al.
(Continued)

FOREIGN PATENT DOCUMENTS

KR 1019980025157 7/1998
WO 2007149533 12/2007
(Continued)

OTHER PUBLICATIONS

PCT International Search Report and Written Opinion, PCT/US2013/063178, filed Oct. 3, 2013, dated Jan. 28, 2014, Korea. 15 pgs.
(Continued)

*Primary Examiner* — James S. McClellan
(74) *Attorney, Agent, or Firm* — John J. Brooks, III

(57) ABSTRACT

In one example embodiment of the invention, a simulation based training system is provided having a sensor that unobtrusively collects objective data for individuals and teams experiencing training content to determine the cognitive states of individuals and teams; time-synchronizes the various data streams; automatically determines granular and objective measures for individual cognitive load (CL) of individuals and teams; and automatically determines a cognitive load balance (CLB) and a relative cognitive load (RCL) measure in real or near-real time. Data is unobtrusively gathered through physiological or other activity sensors such as electroencephalogram (EEG) and electrocardiogram (ECG) sensors. Some embodiments are further configured to also include sociometric data in the determining cognitive load. Sociometric data may be obtained through the use of sociometric badges. Some embodiments further automatically customize the simulation content by automatically selecting content based on the CL of the individuals and teams.

20 Claims, 14 Drawing Sheets

Related U.S. Application Data

(60) Provisional application No. 62/437,583, filed on Dec. 21, 2016.

(51) Int. Cl.
*G09B 7/10* (2006.01)
*G09B 19/00* (2006.01)
*A61B 5/0245* (2006.01)
*A61B 5/369* (2021.01)

(56) References Cited

U.S. PATENT DOCUMENTS

| | | |
|---|---|---|
| 5,727,128 A | 3/1998 | Morrison |
| 5,845,254 A | 12/1998 | Lockwood et al. |
| 6,012,034 A | 1/2000 | Hamparian et al. |
| 6,272,480 B1 | 8/2001 | Tresp et al. |
| 6,379,301 B1 | 4/2002 | Worthington et al. |
| 6,544,212 B2 | 4/2003 | Galley et al. |
| 6,572,545 B2 | 6/2003 | Knobbe et al. |
| 6,582,366 B1 | 6/2003 | Porumbescu |
| 6,601,053 B1 | 7/2003 | Schaffer et al. |
| 6,658,396 B1 | 12/2003 | Tang et al. |
| 6,882,940 B2 | 4/2005 | Potts et al. |
| 6,923,763 B1 | 8/2005 | Kovatchev et al. |
| 6,931,327 B2 | 8/2005 | Goode, Jr. et al. |
| 7,025,425 B2 | 4/2006 | Kovatchev et al. |
| 7,052,472 B1 | 5/2006 | Miller et al. |
| 7,230,529 B2 | 6/2007 | Ketcherside, Jr. et al. |
| 7,296,005 B2 | 11/2007 | Minamino et al. |
| 8,655,822 B2 | 2/2014 | Levchuk et al. |
| 8,762,306 B2 | 6/2014 | Cameron et al. |
| 9,076,107 B2 | 7/2015 | Cameron et al. |
| 10,783,801 B1 | 9/2020 | Beaubien et al. |
| 11,081,234 B2 | 8/2021 | Pappada |
| 2003/0028089 A1 | 2/2003 | Galley et al. |
| 2003/0060690 A1 | 3/2003 | Jelliffe et al. |
| 2003/0153821 A1 | 8/2003 | Berner et al. |
| 2003/0175806 A1 | 9/2003 | Rule et al. |
| 2004/0167418 A1 | 8/2004 | Nguyen et al. |
| 2005/0119540 A1 | 5/2005 | Potts et al. |
| 2005/0119534 A1 | 6/2005 | Trost et al. |
| 2005/0171503 A1 | 8/2005 | Berghe et al. |
| 2005/0197554 A1 | 9/2005 | Polcha |
| 2005/0234311 A1 | 10/2005 | Kouchi et al. |
| 2005/0245878 A1 | 11/2005 | Mernoe et al. |
| 2006/0264718 A1 | 11/2006 | Ruchti et al. |
| 2007/0032706 A1 | 2/2007 | Kamath et al. |
| 2007/0078680 A1 | 4/2007 | Wennberg |
| 2007/0208246 A1 | 9/2007 | Brauker et al. |
| 2008/0027292 A1 | 1/2008 | Rosman et al. |
| 2008/0033254 A1 | 2/2008 | Kamath et al. |
| 2008/0082323 A1 | 4/2008 | Bai et al. |
| 2008/0189051 A1 | 8/2008 | Goode et al. |
| 2008/0221923 A1 | 9/2008 | Shogan |
| 2008/0281170 A1 | 11/2008 | Eshelman et al. |
| 2008/0294019 A1 | 11/2008 | Tran |
| 2008/0306353 A1 | 12/2008 | Douglas et al. |
| 2009/0105573 A1 | 4/2009 | Malecha et al. |
| 2009/0150183 A1 | 6/2009 | Schmitt et al. |
| 2009/0156924 A1 | 6/2009 | Shariati et al. |
| 2009/0163776 A1 | 6/2009 | Inbar |
| 2009/0177143 A1 | 7/2009 | Markle et al. |
| 2009/0192366 A1 | 7/2009 | Mensinger et al. |
| 2009/0192722 A1 | 7/2009 | Shariati et al. |
| 2009/0305214 A1 | 12/2009 | Pybus et al. |
| 2010/0114237 A1 | 5/2010 | Giftakis et al. |
| 2010/0280348 A1 | 11/2010 | Wenzel et al. |
| 2010/0291604 A1 | 11/2010 | Rosman et al. |
| 2010/0292634 A1 | 11/2010 | Kircher et al. |
| 2010/0324936 A1 | 12/2010 | Vishnubhatla et al. |
| 2011/0016067 A1 | 1/2011 | Levchuk et al. |
| 2011/0178820 A1 | 7/2011 | Soni et al. |
| 2011/0225112 A1 | 9/2011 | Cameron et al. |
| 2012/0265549 A1 | 10/2012 | Virolainen |
| 2012/0277833 A1 | 11/2012 | Gerber et al. |
| 2013/0293844 A1 | 11/2013 | Gross et al. |
| 2013/0317834 A1 | 11/2013 | Ryan et al. |
| 2014/0304204 A1 | 10/2014 | Cameron et al. |
| 2015/0012844 A1 | 1/2015 | Paulik et al. |
| 2015/0025329 A1 | 1/2015 | Amarasingham et al. |
| 2015/0095056 A1 | 4/2015 | Ryan et al. |
| 2015/0193583 A1 | 7/2015 | McNair et al. |
| 2015/0227710 A1 | 8/2015 | Pappada |
| 2015/0248613 A1 | 9/2015 | Harris et al. |
| 2018/0168516 A1 | 6/2018 | Pappada et al. |

FOREIGN PATENT DOCUMENTS

| | | |
|---|---|---|
| WO | 2008131224 | 10/2008 |
| WO | 2010019919 | 2/2010 |
| WO | 2011/060398 A1 | 5/2011 |
| WO | 2013126144 | 8/2013 |
| WO | 2014055718 | 4/2014 |
| WO | 2017027432 | 2/2017 |

OTHER PUBLICATIONS

Chubb, Mikayla, Office Action Detail for U.S. Appl. No. 13/058,673, filed Feb. 11, 2011, dated Jul. 25, 2013, USA. 24 pgs.

PCT International Search Report and the Written Opinion, PCT/US2009/53943 filed Aug. 14, 2009, dated Dec. 24, 2009, 6 pgs.

PCT International Preliminary Report on Patentability, PCT/US2009/53943 filed Aug. 14, 2009, dated Feb. 24, 2011, 14 pgs.

Ivanov et. al. 'Temporal Processing Neural Networks for Speech Recognition' In: International Conference on Neural Networks and Artificial Intelligence. Fig. 2 and p. 4, col. 1, para (4), p. 5, col. 1, para (2), p. 7, col. 1, para (7), and p. 8, col. 1, para (4), 9 pgs.

Magoulas et. al. 'Effective Backpropagation Training with Variable Stepsize'. Neural Networks, vol. 10, No. 1, pp. 69-82, 1997, 14 pgs.

Skevolifakas et. al. A Communication and Information Technology Infrastructure for Real Time Monitoring and Management of Type 1 Diabetes Patients. In: Engineering in Medicine and Biology Society, 2007. Aug. 22-26, 2007 pp. 3685-3688.

Pappada, Scott et. al. "Neural Network Prediction of Glucose in Diabetic Patients Using Continuous Glucose Monitoring (CGM) and an Electronic Intensive Life Event Diary (EILED)", 2006, Department of Bioengineering, University of Toledo, Toledo, Ohio and Northeastern Ohio Universities College of Medicine, Rootstown, Ohio, one (1) page poster, USA.

Chubb, Mikayla, Notice of Allowance and Fees Due, U.S. Appl. No. 13/058,673, dated Jan. 31, 2014, USPTO, Arlington VA, USA, 6 pgs.

Chubb, Mikayla, Notice of Allowance and Fees Due, U.S. Appl. No. 14/284,975, filed May 22, 2014, dated Mar. 10, 2015, USPTO, US, p. 10.

Chubb, Mikayla, Office Action Summary, U.S. Appl. No. 14/284,975, filed May 22, 2014, dated Nov. 5, 2014, 11 pgs.

Becamel, Philippe, International Preliminary Report on Patentability, parent PCT App. No. PCT/US13/063178, dated Apr. 7, 2014, Switzerland, 11 pgs.

Klaus Prank et. al. Predictive neural networks for learning the time course of blood glucose levels. Neural Comp, 1998; 10(4):941-953. Entire document, especially Figs. 1-2 and p. 943, para (2), p. 944, para (4), p. 945, para (1), p. 950, para (3), Cambridge MA, USA, 13 pgs.

Volker Tresp et al., Neural Network Models for the Blood Glucose Metabolism of a Diabetic, IEEE Transaction on Neural Networks, Sep. 1999, vol. 10 Issue 5, Piscataway NJ, USA, 24 pgs.

Wong, Lee W., Written Opinion of the International Searching Authority, PCT App. No. PCT/US16/45938, dated Oct. 24, 2016, 14 pages, US.

Patel, Neha, Office Action Summary, U.S. Appl. No. 14/433,501, filed Apr. 30, 2015, dated Sep. 15, 2017, 26 pgs.

Patel, Neha, Office Action Summary, U.S. Appl. No. 14/433,501, filed Apr. 30, 2015, dated Mar. 8, 2018, 33 pgs.

Ferrer, Richard et. al. "Empiric Antibiotic Treatment Reduces Mortality in Severe Sepsis and Septic Shock From the First Hour:

(56) References Cited

OTHER PUBLICATIONS

Results From a Guideline-Based Performance Improvement Program*", Crit Care Med. Aug. 2014;42(8):1749-55, USA, 7 pgs.

Henry, Katharine et. al. "A targeted real-time early warning score (TREWScore) for septic shock", Science Translational Medicine Aug. 5, 2015: vol. 7, Issue 299, p. 299ra122, 10 pgs.

Donegan, Lee-Ann, "Penn Medicine's "Sepsis Sniffer" Generates Faster Sepsis Care and Suggests Reduced Mortality", Perelman School of Medicine, Pennsylvania, USA, 2 pgs.

Klein, K. J., & Kozlowski, S. W. (2000). A multilevel approach to theory and research in organizations: Contextual, temporal, and emergent processes. In K. J. Klein & S. W. J. Kozlowski (Eds.), Multilevel theory, research, and methods in organizations: Foundations, extensions, and new directions (pp. 3-90). San Francisco, CA: Jossey-Bass. 45 pgs.

Evans, J. S. B. T., & Stanovich, K. (2013). Dual-process theories of higher cognition: Advancing the debate. Perspectives in Psychological Science, 8(3), 223-241. 19 pgs.

Olguín, D. O., Waber, B. N., Kim, T., Mohan, A., Ara, K., & Pentland, A. (2009). Sensible organizations: Technology and methodology for automatically measuring organizational behavior. IEEE Transactions on Systems, Man, and Cybernetics, Part B (Cybernetics), 39(1), 43-55. 13 pgs.

Kamzanova, A. T., Kustubayeva, A. M., & Matthews, G. (2014). Use of EEG workload indices for diagnostic monitoring of vigilance decrement. Human factors, 56(6), 1136-1149. 14 pgs.

Berka, C., Levendowski, D. J., Lumicao, M. N., Yau, A., Davis, G., Zivkovic, V. T., & Craven, P. L. (2007). EEG correlates of task engagement and mental workload in vigilance, learning, and memory tasks. Aviation, space, and environmental medicine, 78(5), B231-B244. 14 pgs.

Kohlmorgen, J., Dornhege, G., Braun, M., Blankertz, B., Müller, K. R., Curio, G., & Kincses, W. (2007). Improving human performance in a real operating environment through real-time mental workload detection. Toward Brain-Computer Interfacing, 409-422. 14 pgs.

Moreno, R. (2010). Cognitive load theory: More food for thought. Instructional Science, 38(2), 135-141. 7 pgs.

Gaba, D. M., & Raemer, D. (2007). The tide is turning: organizational structures to embed simulation in the fabric of healthcare. Simul Healthcare 2007;2: 1-3. 3 pgs.

Niehaus, J., & Riedl, M. O. (2009). Scenario adaptation: An approach to customizing computer-based training games and simulations. In Proceedings of the AIED 2009 Workshop on Intelligent Educational Games (vol. 3, pp. 89-98). 10 pgs.

Paas, F., Renkl, A., & Sweller, J. (2003). Cognitive load theory and instructional design: Recent developments. Educational psychologist, 38(1), 1-4. 4 pgs.

Vygotsky, L. (1978). Interaction between learning and development. Readings on the development of children, 23(3), 34-41. 7 pgs.

Ivanova, A., & Dyankova, E. (2009) Designing a Decision Engine for Adaptive Training Simulators. Proceedings of e-Learning, 9, 207-213. 7 pgs.

Olguin, D. O., Gloor, P. A., & Pentland, A. S. (2009). Capturing individual and group behavior with wearable sensors. In Proceedings of the 2009 aaai spring symposium on human behavior modeling, SSS (vol. 9). 7 pgs.

Olguín-Olguín, D., & Pentland, A. (2010). Sensor-based organisational design and engineering. International Journal of Organisational Design and Engineering, 1(1-2), 69-97. 29 pgs.

Salas, Eduardo, Rosen, Michael A., Held, Janet D., Weissmuller, Johnny J. (2009) Performance Measurement in Simulation-Based Training: A Review and Best Practices Simulation Gaming 2009. 49 pgs.

Gevins, A., & Smith, M. E. (2003). Neurophysiological measures of cognitive workload during human-computer interaction. Theoretical Issues in Ergonomics Science, 4(1-2), 113-131. 20 pgs.

Lei, S., & Roetting, M. (2011). Influence of task combination on EEG spectrum modulation for driver workload estimation. Human factors, 53(2), 168-179. 12 pgs.

Funke, G. J., Knott, B. A., Salas, E., Pavlas, D., & Strang, A. J. (2012). Conceptualization and measurement of team workload: A critical need. Human Factors, 54(1), 36-51. 16 pgs.

Oser, R. L., Cannon-Bowers, J. A., Salas, E., & Dwyer, D. J. (1999). Enhancing human performance in technology-rich environments: Guidelines for scenario-based training. Human Technology Interaction in Complex Systems, 9, 175-202. 28 pgs.

Pappada SM, Feeney JJ, Moffat-Bruce SM., Winfield S, Papadimos TJ, A novel measurement technology to improve critical care provider performance and skill acquisition, Society of Critical Care Medicine 46th Critical Care Congress Honolulu, HI, Jan. 2017. 9 pgs.

Pappada SM, Papadimos TJ, Lipps J, Feeney JJ, Durkee KT, Galster SM, Winfield S, Pfeil S, Dastellon-Larios K, Bhandary SB, Stoicea N, Moffat-Bruce SM. Establishing an instrumented environment for simulation-based training of healthcare providers: an initial proof of concept. International Journal of Academic Medicine, Jul. 2016. 124 pgs.

Patel, Neha, Office Action Detail for U.S. Appl. No. 14/433,501, filed Apr. 3, 2015, dated Jan. 17, 2019, USA. 26 pgs.

Reichert, Rachelle, Office Action Detail for U.S. Appl. No. 14/433,501, filed Apr. 3, 2015, dated Aug. 21, 2019, USA. 28 pgs.

Reichert, Rachelle, Advisory Action Detail for U.S. Appl. No. 14/433,501, filed Apr. 3, 2015, dated Nov. 14, 2019, USA. 4 pgs.

Tervonen et al., "A Stochastic multicriteria model for evidence-based decision making in drug benefit-risk analysis", Statistics in Medicine, vol. 30, pp. 1419-1428, Jan. 26, 2011.

Chubb, Mickayla, Restriction Requirement for U.S Pat. U.S. Appl. No. 13/058,673, filed Feb. 11, 2011, dated Apr. 9, 2013, USA. 7 pgs.

Pappada et al., Response to Non-Final Rejection with Affidavit for U.S. Appl. No. 13/058,673, dated Nov. 25, 2013, 73 pgs., USPTO, Arlington, VA, 73 pages.

Reichert, Rachelle, Advisory Action Detail for U.S. Appl. No. 14/433,501, filed Apr. 3, 2015, dated Jun. 8, 2018 USA. 5 pgs.

Reichert, Rachelle, Office Action Detail for U.S. Appl. No. 14/433,501, filed Apr. 3, 2015, dated May 29, 2020, USA. 31 pgs.

Reichert, Rachelle, Office Action Detail for U.S. Appl. No. 14/433,501, filed Apr. 3, 2015, dated Dec. 9, 2020, USA. 34 pgs.

Reichert, Rachelle, Notice of Allowance for U.S. Appl. No. 14/433,501, filed Apr. 3, 2015, dated Mar. 30, 2021, USA. 17 pgs.

Sherwin, Ryan W. Non-Final Office Action, U.S. Appl. No. 15/739,460, filed Dec. 22, 2017, dated Jun. 8, 2021. 18 pgs.

Sherwin, Ryan W., Notice of Allowance, U.S. Appl. No. 15/739,460, filed Dec. 22, 2017, dated Feb. 23, 2022. 10 pgs.

McClellan, James, Non-Final Office Action, parent U.S. Appl. No. 15/850,998, filed Dec. 21, 2017, dated Feb. 5, 2020. 14 pages.

McClellan, James, Notice of Allowance, parent U.S. Appl. No. 15/850,998, filed Dec. 21, 2017, dated May 14, 2020. 5 pages.

Wittan-Regis, Agnes, International Preliminary Report on Patentability for International Pat. App. No. PCT/US2016/045938, dated Feb. 22, 2018. 8 pgs.

Sherwin, Ryan W., Notice of Allowance, U.S. Appl. No. 15/739,460, filed Dec. 22, 2017, dated May 11, 2022. 5 pgs.

FIG. 7

| Subject | Self Report (SR): NASA TLX | Avg Model Output (AMO) | Absolute Diff \|SR-AMO\| | Second by Second Model Classification Accuracy (%) |
|---|---|---|---|---|
| 1 | 23.3 | 50.6 | 27.3 | 75.4 |
| 1 | 58.3 | 44.0 | 14.3 | 85.0 |
| 1 | 56.7 | 47.2 | 9.5 | 83.6 |
| 1 | 64.0 | 56.8 | 7.2 | 88.0 |
| 2 | 73.9 | 74.8 | 0.9 | 92.9 |
| 2 | 91.7 | 67.7 | 24.0 | 89.1 |
| 2 | 84.4 | 75.5 | 8.9 | 94.8 |
| 2 | 98.7 | 77.5 | 21.2 | 98.6 |
| 3 | 46.6 | 41.0 | 5.6 | 100.0 |
| 3 | 64.0 | 41.9 | 22.1 | 80.7 |
| 3 | 20.5 | 46.4 | 25.9 | 85.9 |
| 3 | 62.0 | 49.4 | 12.6 | 94.2 |
| 5 | 36.5 | 51.1 | 14.6 | 90.1 |
| 5 | 42.9 | 64.1 | 21.2 | 76.1 |
| 5 | 48.6 | 57.1 | 8.5 | 85.4 |
| 5 | 77.5 | 55.4 | 22.1 | 73.2 |
| 6 | 50.0 | 79.5 | 29.5 | 36.7 |
| 6 | 56.7 | 82.2 | 25.5 | 37.9 |
| 6 | 47.8 | 85.3 | 37.5 | 20.5 |
| 6 | 70.5 | 83.0 | 12.5 | 74.4 |
| Mean | N/A | N/A | 17.5 | 78.1 |

FIG. 9

SIMULATION BASED TRAINING SYSTEM FOR MEASUREMENT OF COGNITIVE LOAD TO AUTOMATICALLY CUSTOMIZE SIMULATION CONTENT

CROSS-REFERENCE TO RELATED APPLICATIONS

This application is a continuation of U.S. patent application Ser. No. 15/850,998 filed on Dec. 21, 2017; U.S. patent application Ser. No. 15/850,998 claims benefit to U.S. Pat. App. No. 62/437,583 filed Dec. 21, 2016; and the entire contents of both are incorporated by reference in their entirety.

STATEMENT REGARDING FEDERALLY SPONSORED RESEARCH OR DEVELOPMENT

This invention was made with government support under Contract No. W81XWH-14-C-0021 awarded by the U.S. Army. The government has certain rights in the invention.

REFERENCE TO SEQUENCE LISTING, A TABLE, OR A COMPUTER PROGRAM LISTING COMPACT DISC APPENDIX

Not Applicable.

BACKGROUND OF THE INVENTION

1. Field of the Invention

This invention relates to training simulators, in particular a computer-based training simulator with tools to assess the cognitive load of one or more users.

2. Description of the Prior Art

Heart rate variability, oculomotor activity (EOG), pupilometry, functional near infrared imaging (fNIR) and galvanic skin response have been employed to detect cognitive state changes; however, the electroencephalogram (EEG) is the only physiological signal that has been shown to accurately reflect subtle shifts in alertness, attention and workload that can be identified and quantified on a second-by-second time-frame. Significant correlations between EEG indices of cognitive state changes and performance have been reported based on studies conducted in laboratory, simulation and operational environments.

Simulation Based Training (SBT) is used in many branches of medicine—including emergency medicine, surgery, cardiology, and pediatrics, among others—and there are simulation platforms for initial skill acquisition and ongoing maintenance of certification. For example, in emergency medicine there are simulators for practicing basic lifesaving skills (Resusci® Anne); for performing "mock codes" on expectant mothers (Noelle™) and their newborns (SimNewB™); and for practicing advanced combat lifesaving skills on wounded Soldiers (Multiple Amputee Trauma Trainer™). In surgery, there are box trainers for practicing basic skills such as cutting and suturing (LapTrainer™); virtual reality (VR) systems for practicing routine surgical procedures such as laparoscopic cholecystectomy (Lap Mentor™); and patient-specific anatomical models that allow surgeons to rehearse a patient's specific case prior to conducting it in vivo (Surgical Theater™).

Although much progress has been made with regard to skill training, substantially less progress has been made with regard to skill and performance assessment. Many assessment methods still use observer-based rating scales with anchors that range from "low" (1) to "high" (5). One problem with this approach is its level of granularity. For example, one could imagine two medical teams performing the same SBT exercise. While both teams could receive identical numerical ratings, the first team could be performing at the extreme upper bound of its capability, while the second could have a substantial amount of reserve capacity that remains unexercised. It is further possible that despite receiving acceptable scores, both teams could walk away from the exercise feeling demoralized. Specifically, the first team might feel overwhelmed by the workload; they might leave doubting their capabilities as healthcare providers. The second team might feel that they were not sufficiently challenged; they might leave questioning the organization's commitment to providing a quality learning experience. Both outcomes must be avoided at all costs.

BRIEF SUMMARY OF THE INVENTION

The following summary is included only to introduce some concepts discussed in the Detailed Description below. This summary is not comprehensive and is not intended to delineate the scope of protectable subject matter, which is set forth by the claims presented at the end.

Given the prior art solutions, modern simulators that are configured to maximize the training effect in real-time, how do they account for real-time data from various sensors to maximize the effect of that training? In particular, how does a simulator capture and quantify indirect measures of the student that may not be directly related to the user's performance but may be very directly tied to the user's ability to learn from the simulation? In particular, how does the simulator use the data from sensors to objectively measure a cognitive load on the user and how does the simulator use that measure to customize the simulation content to maximize the effect of the simulator? For training simulations that train teams of users, the complexity of the problem is compounded by the many possible ways to measure a team of simulator users.

In addition, given the user measures from the simulator, a technical problem also exists in how the simulator selects the next scenario or simulation content for the user. In particular, how does the simulator select the specific scenario or simulation content, from a large database of scenarios or simulation content, which maximizes the effect of the simulator on the user?

To address these technical challenges, the disclosed systems and methods provide a solution that uses sensitive and diagnostic measures of individual and team states to provide data that can be used to assess the cognitive state of individuals and teams in simulators and maximize the effectiveness of simulation-based training. The technical solution defines a data format to be used to translate the raw data from sensors in real-time so that objectively estimates of a cognitive load of the user can be made in real-time. This real-time quantified cognitive load data can then be used to provide feedback to the simulator to allowing for real-time customization of the training simulation. The objective measures may also allow simulators and trainers to increase the effectiveness of post-training After Action Reviews (AARs).

For the challenges presented when measuring the cognitive load of a team of users, team cognitive load models are disclosed that provide objective cognitive loads of the teams given the real-time cognitive load measures from team members.

Some embodiments of the disclosed solution also address the technical challenge of maximizing the effectiveness of the simulation by comparing the cognitive load of the user to a target effectiveness measure and determining the next simulation content to keep the user and simulation within the target effectiveness measure. These effectiveness measures may be used keep the user within an objective "Zone of Proximal Development" to maximize the training effectiveness given the cognitive load of the user.

Some embodiments of the disclosed solution also address the technical challenge of how to maximize the effectiveness of the simulation by objectively selecting content from a learning management system.

In one example embodiment, a processor based method of assessing a workload of a user in a simulator is provided wherein the method comprises determining a first individual cognitive load measure from the first data with an individual cognitive load measure model. In some embodiments, team cognitive load measures are determined.

In one example embodiment, the present system comprises a processor based cognitive load assessment system that unobtrusively collects objective data that can be used to determine individual and team cognitive states; time-synchronizes the various data streams; and automatically calculates measures of team cognitive load (CL), cognitive load balance (CLB) and/or relative cognitive load (RCL) in real or near real time. Data is unobtrusively gathered through physiological or other activity sensors such as electroencephalogram (EEG), electrocardiogram (ECG), and accelerometry sensors. Some embodiments are further configured to include data about team communications—such as conversational turn-taking, interruptions, and dysfluencies using audio sensors and/or sociometric badges—when determining cognitive loads. Some embodiments may also use sensors that detect heart rate variability, oculomotor activity (EOG), pupilometry, functional near infrared imaging (fNIR) or galvanic skin response.

Some embodiments are further configured to send alerts to a user interface, such as a handheld device, if a threshold of cognitive load is met. Using this real or near-real time assessment and/or alerts, instructors can dynamically modify their team training scenarios on the fly. For example, if the team is overwhelmed (in a "Zone of Confusion"), the instructor or training system could reduce the complexity of the problem (through the training scenario or content) or expand the team size, for example by calling in additional team members. Alternatively, if the team is underwhelmed (in a "Zone of Boredom"), the instructor could increase the complexity of the problem, or reduce the size of the team, for example by having one of the team members unexpectedly leave the simulation or by adding another simultaneous task into the simulation. Until recently, this capability has not been possible. Rather, the common method of modifying training was to help the instructor select the next most appropriate training scenario. Given that scenario-based training—especially team training—can be extremely costly, the approach of automatically assessing cognitive load and dynamically modifying scenarios in real time holds a great deal of promise for the training community-at-large.

BRIEF DESCRIPTION OF THE SEVERAL VIEWS OF THE DRAWINGS

In order that the manner in which the above-recited and other advantages and features of the invention are obtained, a more particular description of the invention briefly described above will be rendered by reference to specific embodiments thereof which are illustrated in the appended drawings. Understanding that these drawings depict only typical embodiments of the invention and are not therefore to be considered to be limiting of its scope, the invention will be described and explained with additional specificity and detail through the use of the accompanying drawings in which:

FIG. 7 illustrates an example embodiment of an observer rating tool user interface with cognitive load altering functionality;

FIG. 9 illustrates a comparison of the ACLAMATE model performance to self-reported measures.

DETAILED DESCRIPTION OF THE INVENTION

Figure 1A:
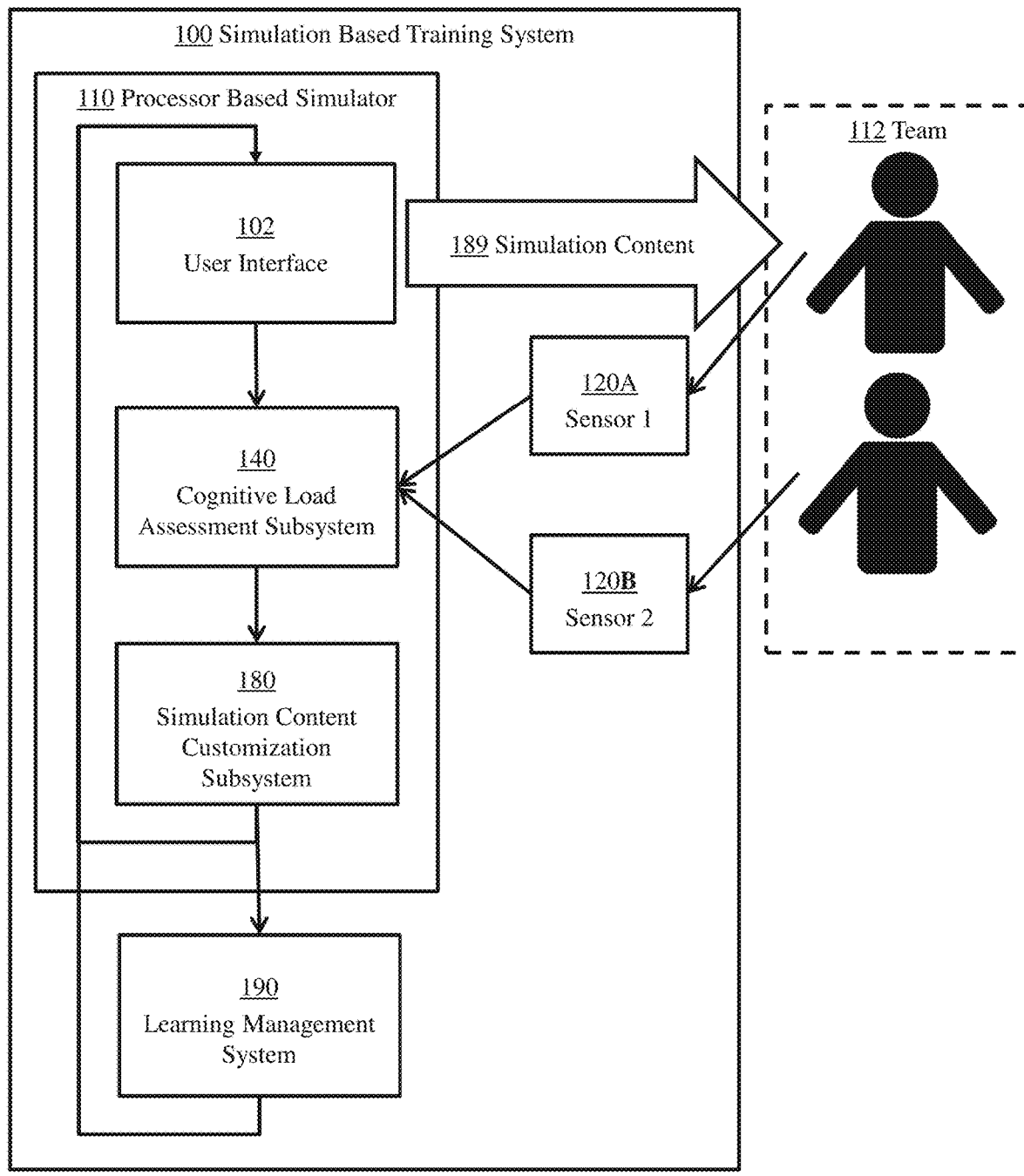
FIG. 1A shows a high level functional diagram of a simulation based training system for assessing cognitive loads of an individual or a team.

Cognitive load assessment tools and simulation based training systems for measuring team cognitive load to automatically customize simulation content will now be described in detail with reference to the accompanying drawings. It will be appreciated that, while the following description focuses on systems and methods that can be used with a computer based simulator for surgical training, some embodiments of the systems and methods disclosed herein may have wider applicability. For example only and not for limitation, some embodiments of the cognitive load assessment tools described herein may be readily employed with health monitoring, individual and team workload monitoring outside of simulators and real-time individual and team training. Notwithstanding the specific example embodiments set forth and claimed below, all such variations and modifications that would be envisioned by one of ordinary skill in the art are intended to fall within the scope of this disclosure.

Fortunately, recent technological advances, such as the development of portable EEG monitors, have now made it possible to assess individual and team states in real time. Within the field of human factors psychology, EEG-based assessments of cognitive workload enjoy widespread use. For example, they have been used during experimental studies on vigilance, human-computer interaction, and motor vehicle safety. Unfortunately, a common limitation among all these efforts is that they been used entirely for assessment purposes. To date, no attempts have been made to provide real-time feedback to instructors or to the training simulators themselves, for example, so that training scenarios can be dynamically modified or customized on-the-fly. Nor have the data been used during a post-training After Action Review (AAR) to facilitate an understanding of performance learned during training. Current subjective methods for assessing workload are problematic in that they either 1) interrupt the trainee to get an estimate of the workload or 2) they make the assessment after the training retrospectively. The disclosed simulation based training systems determines real-time sensor based estimates of individual and team workloads that can support dynamically changing training scenarios based on these workload measures as well as using these measures to enhance the AAR process.

A First Technical Problem and Technical Solution:

Given this situation in the field of training technologies, and the desire to maximize the effectiveness of computer based simulators, several technical problems are presented for computer based simulators. An initial technical problem is, given the real-time data from a simulator, how does the simulation system translate real-time raw sensor data to a format or language that can be easily translated into objective measures to accurately measure the state of the user, particularly the cognitive state of one or more users?

A problem exists in that there are theoretical and empirical challenges when attempting to aggregate individual-level measures to the team level, especially when the measures are not based on a substantive theory of team performance. Psychological constructs, such as workload or intelligence do not necessarily demonstrate isomorphism across levels of analysis. For example, even though intelligence is the single best predictor of individual job performance, it does not necessarily follow that teams with (on average) extremely high levels of intelligence will outperform teams with (on average) lower levels of intelligence. Therefore, in order to fully understand collective phenomena such as team performance, one must measure individual traits and characteristics (e.g., EEG-based measures of individual cognitive load), the interactions among group members over time (e.g., theoretically derived measures of team cognitive load that include EEG- and sociometric data), and relevant contextual factors (e.g., simulator output, expert observer ratings) that may shape the expression of individual and team level phenomena.

Aggregated EEG based metrics of CL, CLB and RCL can be enhanced by integrating with sociometric measures—which capture aspects of team communications such as a voice's pitch, tone and volume, as well as team members turn-taking, interruptions, and dysfluencies—to provide a richer understanding of team performance. These sociometric variables may be used to predict a number of team-related outcomes and cognitive load metrics.

Furthermore, the measures of team CL should be integrated with other sources of data—such as simulator output, observer-based ratings, and meta-data about team member roles and the mission status—to provide a more holistic assessment of team states and team performance in context. This approach may be used to ensure that the measures are theoretically meaningful and practically interpretable.

There are many benefits from objective measures of individual and team cognitive load. For example, it can be noted that cognitive workload is not synonymous with performance. Because instructors are typically required to assess individual and team performance according to a pre-defined set of competencies (i.e., the Accreditation Council for Graduate Medical Education, the ACGME competencies), those competencies will necessarily drive the scenario design and AAR. Therefore, unobtrusive assessments should help provide information to identify why the team performed effectively or ineffectively on those competencies.

Quantification of cognitive load also provides objective measures that can be used by other system components to provide features such as alarming after a cognitive level threshold is met or to be used as objective metrics to be correlated with other measures such as performance measures.

Another example of the benefit of objective measures of cognitive load is to use the measures to allow simulators to implement features consistent with leading developmental psychology concepts. For example, in the field of developmental psychology, there is a concept called the "Zone of Proximal Development" (ZPD) which represents the difference between the learner's current level of mastery and his or her potential level of mastery. To ensure an optimal learning experience, the training should keep the learner within the ZPD at all times. Too much challenge (the "Zone of Confusion") results in learner frustration; too little (the "Zone of Boredom") results in learner apathy. Ideally, the instructor manually, or the system automatically, keeps the learner in the ZPD by modifying the exercise in real-time using techniques such as scaffolding, Socratic dialogue, content selection, and tutoring to force the learner into a mental state that is characterized by sustained—but not overwhelming—levels of workload, task motivation, and facilitating anxiety. Cognitive Load Theory (CLT) dictates that training should minimize CL so as to not overwhelm the learners' working memory. However, because CL is correlated with learner motivation, minimizing CL can be counterproductive. By contrast, ZPD theory dictates that training should purposely keep the learner's CL sufficiently high to sustain their motivation, but not so high as to overwhelm them. In essence, while CLT proposes negative linear relationship between CL and performance, ZPD theory proposes a curvilinear relationship—an inverted U-shaped curve—between CL and performance. However, our goal is not to minimize CL. Rather, in keeping with Vygotsky's ZPD theory, a goal is to ensure that learners stay in the topmost part of the inverted U-shaped curve, so as to maximize their motivation, learning, and performance during training. Having objective, accurate and real or near real-time measures of cognitive load allow the systems and instructor to know whether the user is in the ZPD in an attempt to keep the learner in the ZPD.

Figure 3:
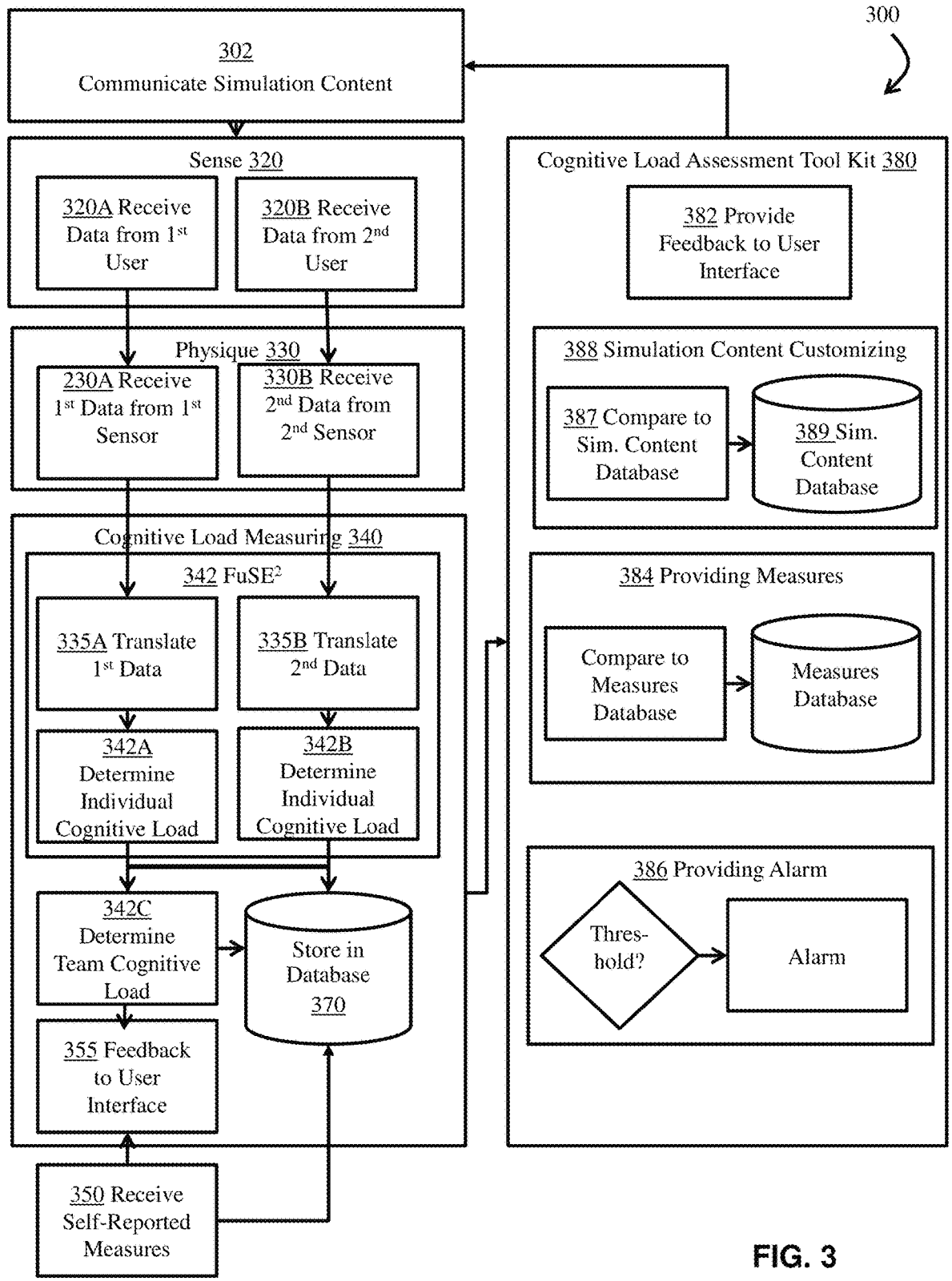
FIG. 3 shows a process diagram illustrating the general concepts of one embodiment of the simulation based training system.

The resulting technical solution to this first technical challenge of objectively measuring cognitive load is to provide systems and methods that use the sensitive and diagnostic measures of the states of individuals and teams to provide data that can be used assess the cognitive state of individuals and teams in simulators. As shown in FIGS. 1A and 3, the technical solution defines a data format that translates the raw data from sensors in real-time so that objectively estimates of a cognitive load of the user can be made in real-time. This real-time cognitive load data can then be used to provide feedback to the simulator to allow for real-time customization of the training simulation, such as increasing the level of difficulty (when the team is in the "Zone of Boredom") or decreasing the level of difficulty (when the team is in the "Zone of Confusion"). The objective measures may also allow simulators and trainers to increase the effectiveness of post-training After Action Reviews (AARs), for example by showing how the team's level of cognitive load led to errors in team performance.

A high level functional diagram of an example embodiment of the technical solution is shown in FIG. 1A. The technical solution comprises a simulation based training system 100 having a processor based simulator 110 that communicates simulation content 189 to individuals and/or teams 190 through a user interface 102 and receives data from the users 112 through sensors 120A and 120B. The sensors 120A and 120B communicate data from the users 112 real time to the cognitive load assessment subsystem 140 that determines objective CL measures for the individuals and/or teams 112. The CL measures may then be used by the simulator and trainers to quantitatively assess or ensure the effectiveness of the training for the users 112. The simulation content may be any type of task or event communicated to a user or team in the simulation. For example and not for limitation, the simulation content may be a single task in a larger training scenario, a particular grouping of users in the simulation or one training scenario from a larger group of scenarios. The simulation content may also be any type of communication outputted to the user as part of the simulation. For example and not for limitation, simulation content may comprise any audio, visual, haptic, tactile or other output communicating portions of the simulation to the user or team. The simulation content may also be a device to communicate simulation content such as unique interfaces to communicate unique content to the user.

For the challenges presented when measuring the cognitive load of a team of users, team cognitive load models are disclosed that provide objective cognitive loads of the teams given the real-time cognitive load measures from team members. Team cognitive load is updated using the current individual members' cognitive load as they change overtime. The team cognitive load can be computed for any team with two or more members.

A Second Technical Problem and Technical Solution:

The state of training simulators and the desire to maximize their effectiveness also presents the challenge of how does the system decide how to customize the training in real-team to maximize the effectiveness of the training? In particular, given the object measures of cognitive load of a user, how does the simulator select the specific simulation content, from a large database of simulation content, that maximizes the effect of the simulator on the user and/or team?

To date, several research groups have attempted to incorporate elements of Vygotsky's ZPD theory in the fields of simulation-based training (SBT) and game based training (GBT). However, these efforts have focused exclusively on selecting the next best training scenario from a library of pre-existing scenarios, rather than dynamically modifying an ongoing scenario in real time. Moreover, neither effort directly assessment of the learners' actual cognitive states using EEG-based methods. Instead, the learners' states were inferred based on task-related outcomes, such as the percentage of correct responses, reaction times, the time it took to complete the scenario, and the like. In short, this work has been stymied by the inability to directly and accurately measure learner cognitive states in real time. Finally, the prior art approaches have the problem of being extremely expensive. Given the substantial costs involved in designing, scheduling, and conducting team training exercises—including the opportunity costs associated with removing a multidisciplinary healthcare team from direct patient care activities so that they can participate in training—it may not be possible to conduct more than one or two SBT exercises per team, per fiscal year. Have training systems that maximize the effectiveness of training in real-time provide a significant improvement to the technology of training systems and methods.

To address this technical challenge of maximizing the effectiveness of the simulation, embodiments of the disclosed systems and methods compare the cognitive load of the entire team (team CL, RCL or CLB) to a target effectiveness measure and determine how to modify the simulation content or scenario to keep the user or team within the target effectiveness measure. These effectiveness measures may keep the user and/or team within an objective "Zone of Proximal Development" to maximize the training effectiveness given the team's or user's cognitive load. The modification of the simulation content may be the changing of simulation tasks within a larger ongoing simulation scenario or it may be a modification of other elements within the scenario such as changes to the simulation environment or changes to the teams in the simulations.

An example of this technical solution is shown in the high-level diagram of FIG. 1A. As shown, with the CL determined by the cognitive load assessment subsystem 140, the simulation content customization subsystem 180 may customize the simulation content 189 presented to the team 112.

As shown in FIGS. 1A and 3, some embodiments of the disclosed solutions may also address the technical challenge of how to maximize the effectiveness of the simulation based training system 100 by objectively selecting simulation content from a learning management system 190 to help provide addition input to determine the simulation content 189.

One Example Embodiment of Simulation Based Training Systems for Measurement of Cognitive Load to Customize Simulation Content:

One purpose of simulation based training systems and automated cognitive load assessment subsystems is to develop technologies for unobtrusively assessing individual and team workload during simulation-based training (SBT). One example embodiment of such as simulation based training system was the ACLAMATE (Automated Cognitive Load Assessment for Medical Staff Training and Evaluation) system. While simulator technologies have advanced greatly, methods for assessing individual and team performance have lagged behind. Today, many trainers still use pencil-and-paper methods, with anchors rating from low (1) to high (5). In complex medical exercises where team members perform specialized roles, such coarse assessments have limited utility. The systems and methods disclosed closed this gap by unobtrusively measuring the cognitive workload of each team member in real-time, as well as measuring the dynamics of the entire team. It then provides real-time alerts to the instructor, who can use this information to modify training scenarios on-the-fly, thereby providing a tailored learning experience. This approach is also extremely cost-effective, given the substantial costs involved in designing, organizing, scheduling, and running team training exercises for an entire organization such as a health care organization.

ACLAMATE addresses the need for unobtrusive, real-time objective measures of individual and team functional states, such individual cognitive load (CL), team cognitive load balance (CLB) and relative cognitive load (RCL). By objectively measuring and informing the instructor or other elements of the training system about changes in team CLB, instructors or the system itself can modify the training scenario to ensure that the learners stay within the ZPD at all times. In some embodiments, the system can alert the instructor to changes in team CLB, and recommend changes to the training scenario—such as increasing or decreasing the level of difficulty, expanding the team size by bringing in additional team members, and the like. The approach for changing the scenarios can use team and or individual cognitive load measures as well as team and individual performance measures.

In other embodiments, the training system can provide other objective measures of the team CL such as average CL across the team members or the RCL.

In other embodiments, the training system can automatically modify or select the next training content based on predefined or learned set of rules such as those systems disclosed in pending U.S. patent application Ser. No. 15/395,574 filed Dec. 30, 2016 and pending U.S. patent application Ser. No. 14/143,410 filed Dec. 30, 2013 (the "BEST" applications), both of which are herein incorporated by reference in their entirety.

In some embodiments, the ACLAMATE system also includes an alerting tool. In these embodiments, and the system may send "high workload" and "low workload" alerts to an instructor via computer monitor such as a handheld tablet. These alerts can be communicated to the training system to alert instructors or to provide input to the simulation content that is presented to the user.

One embodiment of the ACLAMATE system software architecture (FIG. 1B) consists of a series of several software application modules comprising: (1) a Physique client 130A, (2) a Real-Time Data Management (RTDM) module 144 and a (3) FuSE$^2$ module 142. The RTDM module 144 and the FuSE$^2$ module 142 may reside in a cognitive load assessment subsystem 140 such as a server. The Physique client 130 is charged with acquisition, processing (i.e. filtering, artifact correction, etc.), and deriving useful features (for cognitive load models) from neurophysiological data collected by wireless physiological monitors/sensors 102. The RTDM module 144 is used to start/stop data collection sessions, store data to a local database 170, and receive, and reroute system data to other applications within the software. The other applications within the software architecture may comprise a historical data service module 146 used to playback information such as in an AAR, a video streaming service module 147 used to stream real-time images of the user's performance, and a data streaming service module 148 used to stream real-time data representing the user's metrics and performance. The FuSE$^2$ module 142 is a tool which manages and executes ACLAMATE'S neural network-based cognitive load models 143 (for individual subjects), and provides real-time visualization of features derived from the Physique client 130 and cognitive load model module 143 results.

As also shown, the client module may allow a system user to provide input to or receive data from the cognitive load assessment subsystem. The visualization interface may allow a system use to see data such as a video of the individual or team in the simulation. The SPOTLITE modules may be used to provide self-reported data values or data from a third-party such as an instructor.

Although the system can accommodate any neurophysiological monitoring device, one suitable device is the Neurotechnologies BioRadio 150, which is manufactured by Great Lakes Neurotechnologies in Cleveland, OH. This monitor is able to provide the system with reliable and accurate EEG and ECG signals in real time via a wireless connection. Other suitable monitoring devices may include emerging physiological monitoring technologies such as functional near infrared imaging (fNIR), as well as more low cost and non-invasive technologies such as the Zephyr BioHarness which measures heart rate, respiration rate, galvanic skin response, and other autonomic bodily responses.

Additionally, the observer-based performance measurement application (SPOTLITE) may be launched on an application deployed on an Android tablet and sends measurement results to the RTDM module for storage within the local database and visualization within ACLAMATE's user interfaces as needed.

Cognitive Load Measures:

The ACLAMATE system includes an architecture that is capable of providing configurable, real-time measures of individual and team CL on a 100-point NASA TLX anchored scale using one of or a combination of electroencephalogram (EEG) and electrocardiogram (ECG) data. The architecture was built on an individual-level architecture that was used for the Air Force's HUMAN Laboratory. The architecture was purposely designed with flexibility in mind.

The cognitive load assessment subsystem can be easily adapted to accommodate different model architectures and measurement algorithms, via replacing the current models and measurement algorithms with enhancements such as dynamic linked libraries and Aptima's Human Performance Markup Language (HPML) within Aptima's PM Engine™.

The architecture may be sensor specific or may be sensor agnostic, and can thus accommodate any number of neurophysiological, behavioral, sociometric, performance, and environmental/system monitoring hardware. For example, application programming interfaces (APIs) enable the system to discover and use external plug-ins (e.g., Java JAR files or DLLs) that can be loaded by the system. The data acquired from these plugins will continue to be streamed to other necessary components, and will be stored in the database.

Additionally, the systems and architecture can be extended to measure other functional states such as fatigue, stress, or engagement. Finally, the machine learning algorithms can adapt to individual variations in neurophysiological data over time. As trainees use the system their previous training data and self-reported workload can be used to update a set of weights for the machine learning component. In this way, each trainee can develop individualized models that react and respond to their unique physiology. In some embodiments, this adaptation is made through the learning and modification of different algorithm variables such as but not limited to weights or network weights as described below. As a result, the CL estimates will become increasingly more accurate as additional data is collected from each participant.

Individual CL Measures:

The individual CL model is a time-delay neural network (TDNN). TDNNs store delayed values of each input feature that passes through the network (with a delay of time t between each value). This effectively provides the network with a memory system for storing historical data; it also provides the ability to learn relationships over time. The TDNN is well-suited to model trends in EEG and ECG signals, because they are related to changes in team CL over time.

Figure 1B:
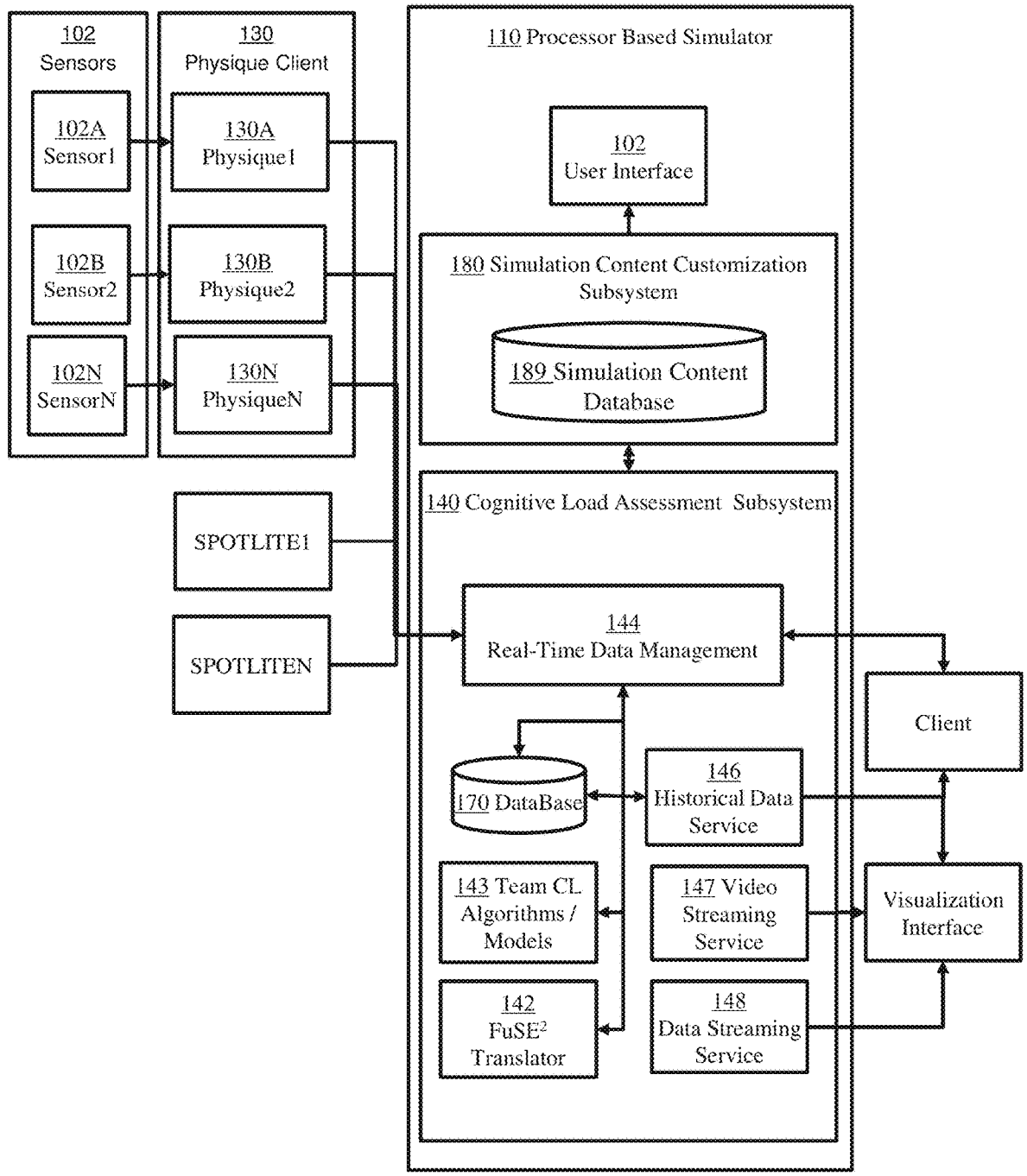
FIG. 1B shows a high level software architecture diagram of a consolidated architecture for assessing cognitive loads.

FIG. 1B depicts the individual CL model as a TDNN. Here, x(t) is the input data stream; it consists of translated data derived from raw EEG and/or ECG signals which are collected from a neurophysiological monitor in real-time. The signals may comprise EEG measures of voltage fluctuations resulting from ionic current within the brain neurons of the user and ECG measures may comprise electrical pulses associated with heartbeats and heart rate of the user. Because the EEG and ECG signals are sampled at different rates, processed features transforms the raw signals into features to be used as the components of x(t) to be time-synchronized. The model output is then pushed out in real-time.

In one embodiment, the data source is an EEG and/or ECG signals and the neural network model is a TDNN. The general form for this TDNN is:

$$y(t) = \left(\sum_{i=1}^{N} w_i \delta_i(t-d_i)\right) * x(t) = \sum_{i=1}^{N} w_i x_i(t-d_i),$$

where y is the resulting predicted values generated (at time t), w is the matrix of network weights, δ is a delta function, d is the time delay, t is time, x represents the input values of the EEG/ECG data source, i represents a number of increments and N represents the number of i inputs to be used in the TDNN. The EEG/ECG data source comprises values for the input data such as, but not limited to a heart rate, electrical activity of the brain such as voltage fluctuation or spectral content ("brain waves") of the EEG. The time delay neural network maintains a history of model inputs via tap delay lines that store a current real-time EEG/ECG input data vector. Tap delay lines allow for prior data to be stored for use with the current data. The neural network also consists of N hidden layers and a single output layer.

In other words, the TDNN takes the value of the EEG/ECG data received as x to predict a value y at a time t. For example, $x_i$ may be one value of the input data received. The TDNN has predefined values for the variables of w, δ and d. For example, w is the computed matrix of weights, δ is the delta function or how much change allocated to the weights and d is the amount of time between the current time and history of the network. The input to the TDNN is x which represents the input vector of the EEG/ECG data received at a time t as described above.

The output of the TDNN is y which represents the computed output of the network from an input vector x at time t as the equation iterates through the N elements of the input vector.

The components of w, δ and d are internal components of the TDNN which are defined above. In this embodiment the output of the TDNN, y represents the cognitive load of the individual trainees. The resulting output of the network can be used to construct an HPML compliant measure representing the CL of individual trainees as well as the team CL measures.

In one embodiment the neural network is trained via backpropagation where optimal network weights (w) for the TDNN equation are identified via a Levenberg-Marquardt algorithm. For example, first the matrix of network weights (w) are initialized to random values. The Levenberg-Marquardt algorithm adjusts these weights with repeated exposure to the training data until an optimal set of weights is computed based on the difference between the predicted value of y and the expected y. The adjustment of these weights is the embodiment of the learning. A set of weights can be updated to provide personalized learning with additional data collected during training. The process is identical as described above except (1) the weights are not reinitialized to random values and (2) the new data collected from the trainee is added to the original training data. In this way, the trainees' performance is reflected in the new set of weights computed.

Suitable embodiments of systems and methods to use EEG, ECG and other physiological measures to determine a user state include those disclosed in U.S. patent application Ser. No. 14/772,827 filed on Sep. 4, 2015 and this application is incorporated herein in its entirety.

The individual CL values from these sensors and algorithms are scaled to a 1-100 scale by taking the raw values computed for y (the output of the network) and performing a linear transformation. Values output for y range from +/−1.0 thus the linear transformation to get CL values scaled from 1-100 are defined by the equation:

$$CL = \frac{(y+1)}{2} * 100 + 1 \qquad [A]$$

The CL values may be scaled from 1-100 to allow for easy comparison with the subject workload scales implemented by the NASA TLX.

Team CL Measures:

The team CL measures provide real-time, second-by-second measures across multiple participants; as such, it allows us to calculate measures of Relative Cognitive Load (RCL) and Cognitive Load Balance (CLB). These two measures are averaged over a configurable N-second time window and are operationalized in Human Performance Markup Language (HPML) and processed using tools such as Aptima's Performance Measurement Engine (PM Engine™) as detailed in U.S. patent application Ser. No. 15/098,216 file on Apr. 13, 2016 entitled "SYSTEMS AND METHODS TO MEASURE PERFORMANCE" which is herein incorporated by reference in its entirety HPML defines a format by which the CL measure can be published or communicated for use in other applications that adhere to the HMPL standard.

To derive the RCL and CLB measures, the second-by-second individual CL measures are filtered and averaged using Equation 1 below:

$$CL(t) = \frac{1}{N} \cdot \sum_{i=0}^{N} CL(t-i) \qquad [1]$$

Measures of team cognitive load at time t ($T_{CL}(t)$) are calculated using Equation 2 below, where M is the number of team members and $CL_i(t)$ represents the filtered cognitive load of team member i at time t:

$$T_{CL}(t) = \frac{1}{M} \cdot \sum_{i=1}^{M} CL_i(t) \qquad [2]$$

The CL represents a measure of the overall team cognitive load. However, the RCL provides insight into how each team member contributed to the team CL. Likewise, the CLB provides a measure of how well the workload is distributed across the team. The RCL could be used to indicate a team member is overloaded whereas the CLB could indicate that the team's CL isn't distributed equally among the team members. The team CL, RCL, and CLB provides a more complete representation of the team's state.

RCL indicates the relative contribution of cognitive load from each team member with respect to the averaged team value. This value can range from +/−100, where an increasing negative value indicates that the team member is under-loaded, and an increasing positive value indicates the team member is over-loaded. Values of RCL are calculated by determining the mathematical distance between CL(t) and $T_{CL}(t)$ relative to an allowable range and bounds based on $d_{max}$ defined in Equation 3 below. In Equation 3, T is defined as a threshold value to define an allowable range of $T_{CL}(t)$ based on T standard deviations from the mean of $T_{CL}(t)$ over the time window N:

$$d_{max} = \frac{1}{N} \cdot \sum_{i=0}^{N} T_{CL}(t-i) + T \cdot \sqrt{\frac{1}{N} \cdot \sum_{i=0}^{N}\left(T_{CL}(t) - \frac{1}{N} \cdot \sum_{i=0}^{N} T_{CL}(t-i)\right)^2} \quad [3]$$

Using $d_{max}$, $RCL_i(t)$ can be calculated separately for each team member i using Equation 4 below:

$$RCL_i(t) = 100 \cdot \left(\frac{CL_i(t) - T_{CL}(t)}{d_{max}}\right) \quad [4]$$

Knowing the RCL of the individual team members would provide insight into the particular team members' individual training needs or provide insight into the underlying reasons for team training performance. The RCL may also be used as an input variable to determine what simulation content should be presented next.

CLB provides an indication of team effectiveness based on the distribution of cognitive load across all team members. CLB ranges from 0-100, where a higher value indicates that workload and tasking are distributed equally across the team, and that no one team member is significantly over- or under-loaded for an extended period of time. Measures of CLB at time t are calculated using measures of $RCL_i(t)$ calculated for each team member (of team size M) over the time window N, as represented in Equation 5 below:

$$CLB(t) = \frac{1}{M} \cdot \sum_{j=1}^{M} 100 - \left|\frac{1}{N} \cdot \sum_{i=0}^{N} RCL_i(t-i)\right| \quad [5]$$

The resulting CLB values are scaled to a 1-100 scale because the absolute values of the individual RCL values are used and it is normalized by the team size M. As values for RCL approach 0 for all team members the value for CLB approaches 100 indicating optimal CLB. As values for RCL deviate from 0 either positively or negatively, the values for CLB decreases from 100 indicating a difference in CLB.

In some embodiments, the CLB measure weights positive and negative values of RCL equally, indicating both under-loaded and over-loaded team members impact the CLB equally. The CLB measure provides insight over the course of the training of how team members are contributing. Depending on the underlying task requirements of the training an unbalanced team workload may be an indicator of issues with the team.

The CLB may also be used as an input variable to determine what simulation content should be presented next.

In some embodiments, the RCL may be weighted differentially. And in some embodiments, the RCL and CLB measures may be revised to account for the varying demands of different team member roles (e.g., nurses or surgeons) and mission phases (e.g., anesthesia induction, initial incision, start of surgical procedure, closing). For example, absent any significant adverse events during the scenario, the anesthesiologist's workload will always be highest prior to the initial incision; it should then decrease markedly before reaching a plateau throughout the remainder of the scenario. Measures of CLB may be expected to take into account different team roles and their effect on CL during the various mission phases by weighting some team members RCL differently than others and accounting for the different weighting at different times. For example, during surgery, the anesthesiologist exhibits the highest levels of workload prior to the initial incision. During this time, the surgeons are discussing their plans for executing the procedure, but there is little that they can do to assist the anesthesiology team. After the patient is fully sedated, the surgeons can begin their work. Therefore, during the pre-incision period, workload should be calculated using the anesthesiology team (e.g., the anesthesiologist and CRNA only). Later, the referent group should be expanded to also include the anesthesiologist, the surgeons and the scrub nurse. Therefore, context is important to calculating and interpreting measures of team workload. Similarly, workload measures may need to be re-calibrated to different referent groups at various points throughout the mission.

Using CL to Automatically Customize Simulation Content:

Embodiments of simulation based training systems that are capable of measuring the cognitive load of users may automatically customize simulation content by modifying or selecting the next simulation content to be provided to the user and/or team.

In these embodiments, measures of RCL and CLB are used as a proxy for the team's overall level of task-related expertise. During the initial stages of skill acquisition, learners rely on explicit rules, strategies, and factual knowledge to solve problems. This imposes a high level of cognitive workload on the learner. As a result, the learner has to consciously monitor their task performance in order to perform the task accurately or correctly. With repeated practice, these rules, strategies, and factual knowledge become more or less automatic in their execution. As a result, learners can perform the task without having to continuously monitor their task performance. As a result, the learners have spare cognitive capacity, which theoretically allows them to perform other tasks simultaneously. Using the methods disclosed in the BEST applications referenced previously, real-time measures of RCL and CLB are used as a proxy for team expertise. The team is first presented with a "medium" difficulty training scenario. If they perform well on the task and experience low levels of workload, they are then presented with a more difficult task during the next training scenario. If they perform poorly on the task and experience high levels of workload, they are presented with a simpler task during the next training scenario.

Example Embodiment of Team-Level Model Architecture with Optional Sociometric Input A notional architecture of a team-level cognitive load model (see FIG. 2B) that extends the team RCL and CLB measures to include sociometric data. A major differentiating factor between the team-level model and the individual cognitive load model are its input features. The team cognitive load model, uses neurophysiological measures of individual cognitive load, RCL, and CLB, and may also use processed feature data collected from the sociometric badges to calculate an enhanced measure of team CL. Examples of suitable sociometric badges include those sold by Humanyze (previously known as Sociometric Solution, Inc.) from Boston, Mass. under the brand of the Sociometric Badge. Other examples of suitable sociometric badges and those disclosed in U.S. patent application Ser. No. 10/839,070 filed on May 4, 2004 which is herein incorporated by reference in its entirety.

Figure 2A:
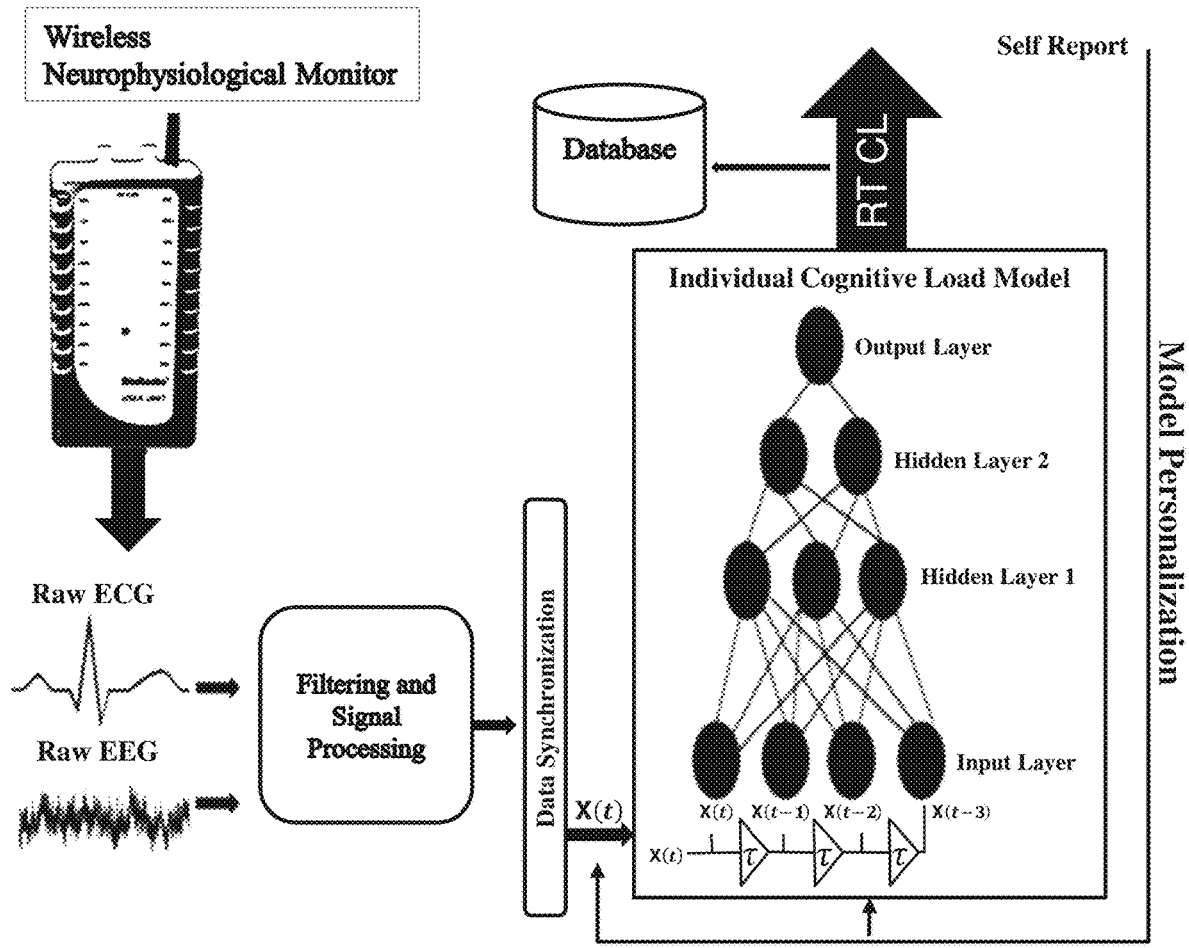
FIG. 2A shows a high level software architecture diagram of an example embodiment of an individual cognitive load model.
Figure 2B:
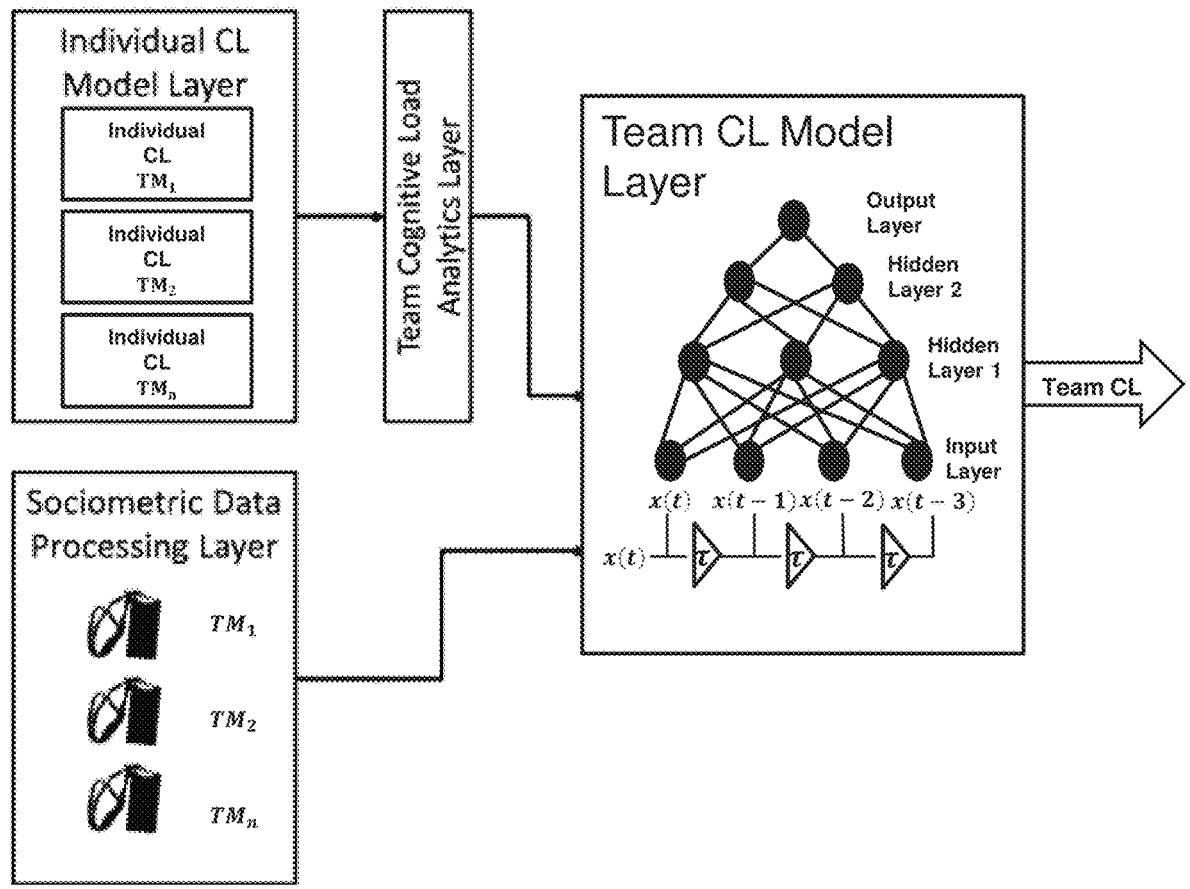
FIG. 2B shows a high level software architecture diagram of an example embodiment of a team cognitive load model.

In some embodiments, as shown in FIG. 2B, there are four layers to the ACLAMATE model:

The first layer is the Individual Cognitive Load Model Layer, which comprises N individual cognitive load models, where a different CL model exists for each team member i ($TM_i$). These models are designed with the same architecture as illustrated in FIG. 2A.

The second layer is the Team Cognitive Load Analytics Layer, which processes the individual measures of RCL and CLB, which are based on the processed EEC and ECG data.

The third layer is the optional Sociometric Data Processing Layer. This layer comprises algorithms that will process data from the sociometric badges to improve the measures of team cognitive load. Potentially useful measures include: honest signals (body movement energy, posture, volume, pitch); elements of conversation (speech/silence, turn taking, interruptions, dysfluencies); and social network characteristics (face-to-face interaction, proximity)

The fourth and final layer is the Team Cognitive Load (CL) Model Layer. This layer comprises a TDNN which leverages data from preceding three layers to classify and provide estimates of team CL vis-á-vis the expert observer ratings gathered using the wireless handheld tool. The team cognitive load model architecture may operate in real-time (like the individual CL model architecture). Additionally, these measures may be displayed on the visualization tool and stored in the database.

Alternative Embodiments of the ACLAMATE System

Initial alerts and notifications may be used to provide alerts when CL levels became too high or low. This was accomplished by developing basic measures in PM Engine that used predefined thresholds to determine whether the average cognitive load (over a configurable time window) was too high or low. These results were then published on the message bus displayed on the handheld device by providing visual alerts next to the source of the data (i.e., a particular team member, or the team as a whole).

The system may also provide for a separate data acquisition module which will allow uploading of non-real-time data into the system so that the data is in a central repository and can be queried for post-hoc visualizations. Having flexible real-time and post-hoc data acquisition functionality is helpful when integrating with additional monitoring. This can include—but is not limited to—additional neurophysiological monitors, the newly developed sociometric badges, patient manikins and surgical simulators, and the like.

The system may also incorporate server-side functionality to accommodate AAR modules for processing and visualizing historical data. These AAR modules are configured to request data stored in the ACLAMATE database. The AAR module may also provide a means to retrospectively estimate team cognitive load measures derived throughout a particular scenario.

Figure 7:
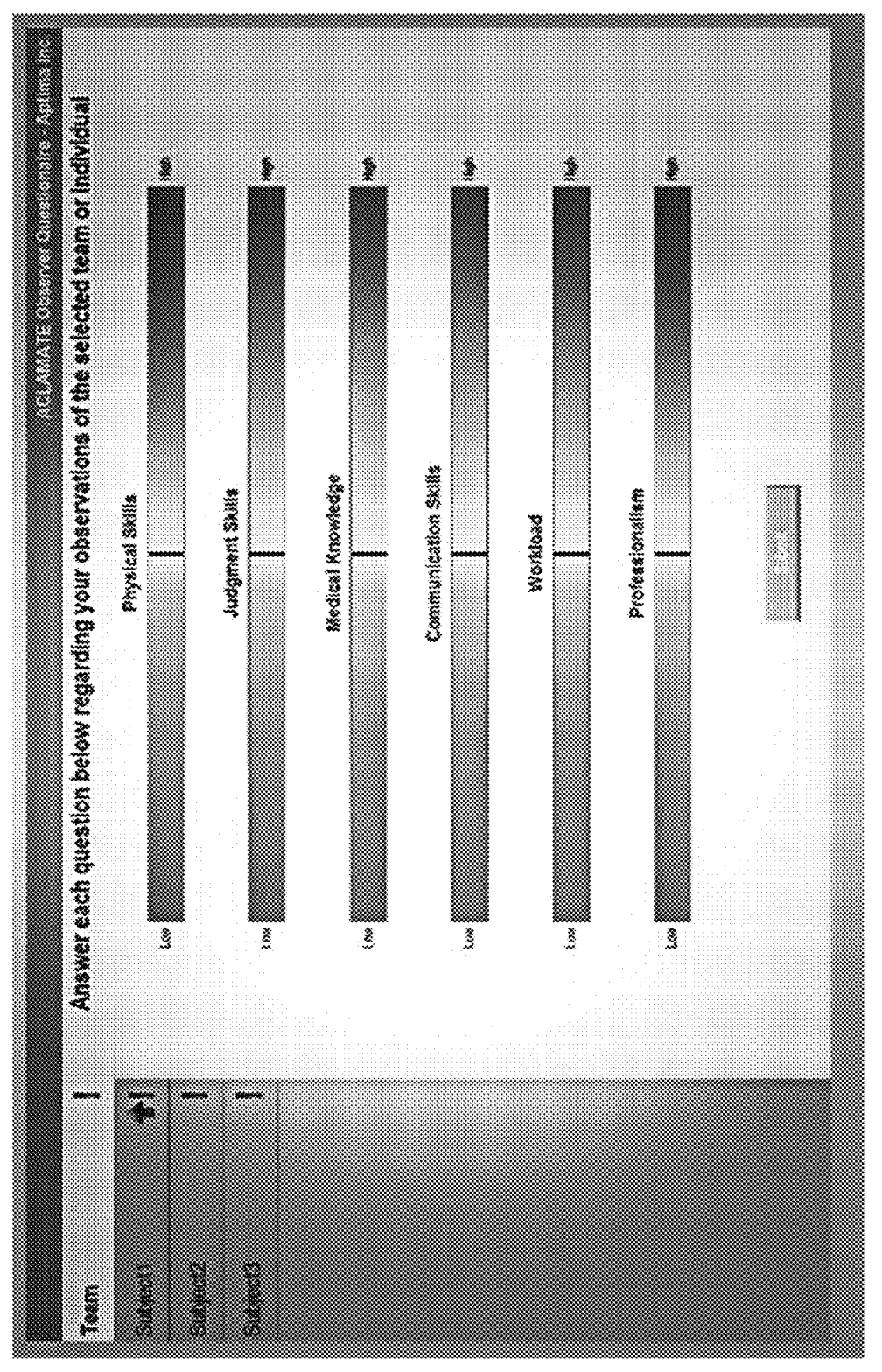

The systems may also incorporate observer-based performance assessment tools that support real or near real-time performance and workload measurement during a scenario. This tool, which operates either on a wireless tablet or a laptop PC, automatically prompts the observer to rate the team's workload every 90 seconds via presenting a flag, such as an exclamation mark, next to the individual or team where a measurement is needed (see left hand side of FIG. 7). The ratings are then pushed to the server for correlation with the unobtrusive measures. The observer-based performance measurement application may include graphical alerts when cognitive load thresholds are exceeded. The alerts generated by ACLAMATE are indicated by a red arrow pointing upwards (for high cognitive load alert) and downwards (for a low cognitive load alert) on the observer-based performance measurement tool user interface as shown below in FIG. 7. In FIG. 7, a high cognitive load alert was displayed for one of the three team members.

Measures of CL and team CL may be made at near real-time (e.g., calculated every 10-15 seconds) or may be made at real-time.

User Interfaces:

The user interface may be any interface suitable for displaying or otherwise communicating the information used by and/or determined by the system. In some embodiments, the interface comprises a large-screen LCD monitors. Example embodiment of information communicated through the user interface includes dashboard designs as shown in FIGS. 2-5.

Figure 4A:
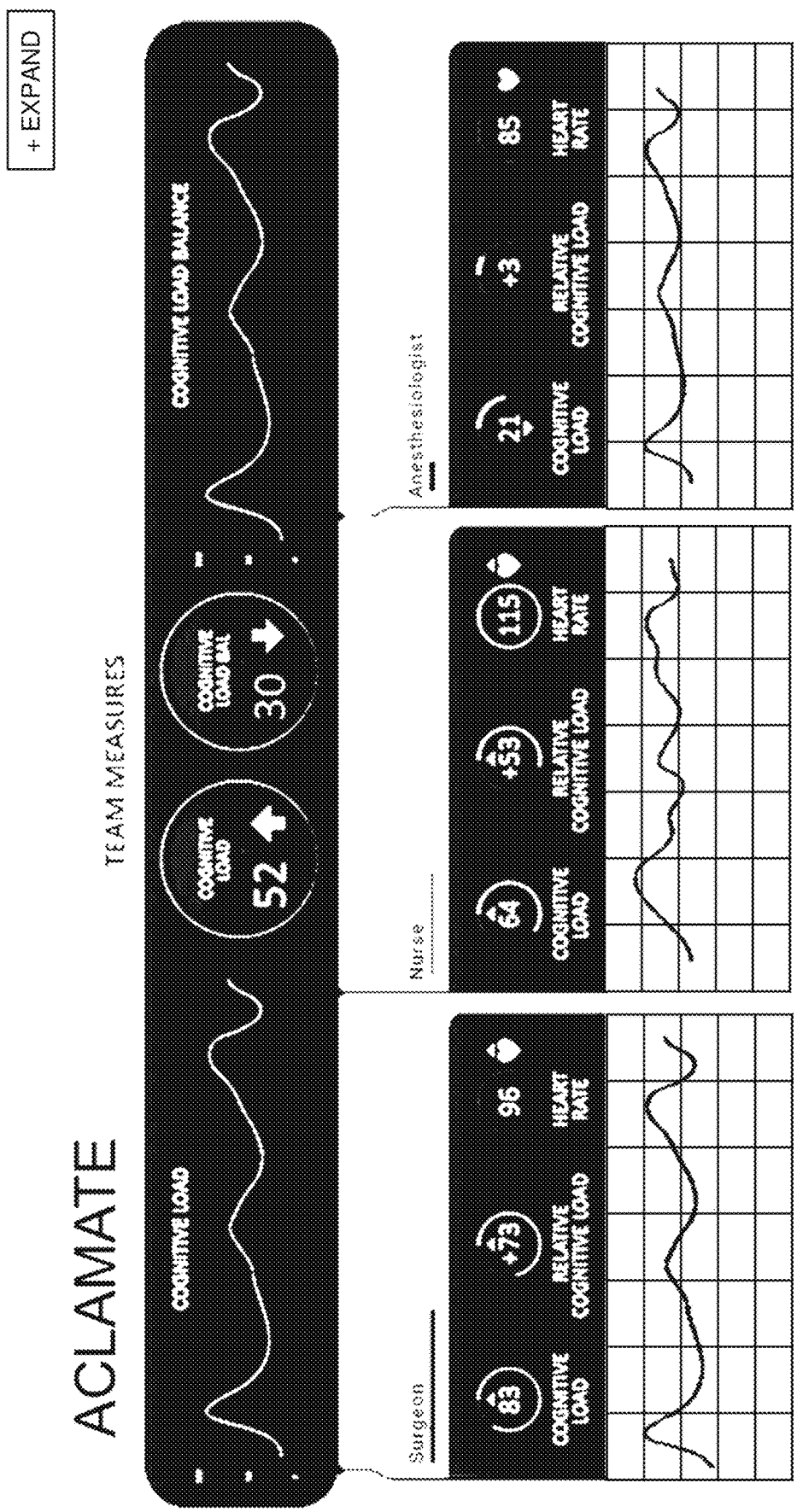
FIG. 4A illustrates an example embodiment of a user interface showing a "quick look" dashboard.

FIG. 4A includes the quick-look dashboard which provides system users a real-time visualization of key system measures and results. This is intended to provide situational awareness to instructors and simulation specialists who are running simulation-based training.

Figure 4B:
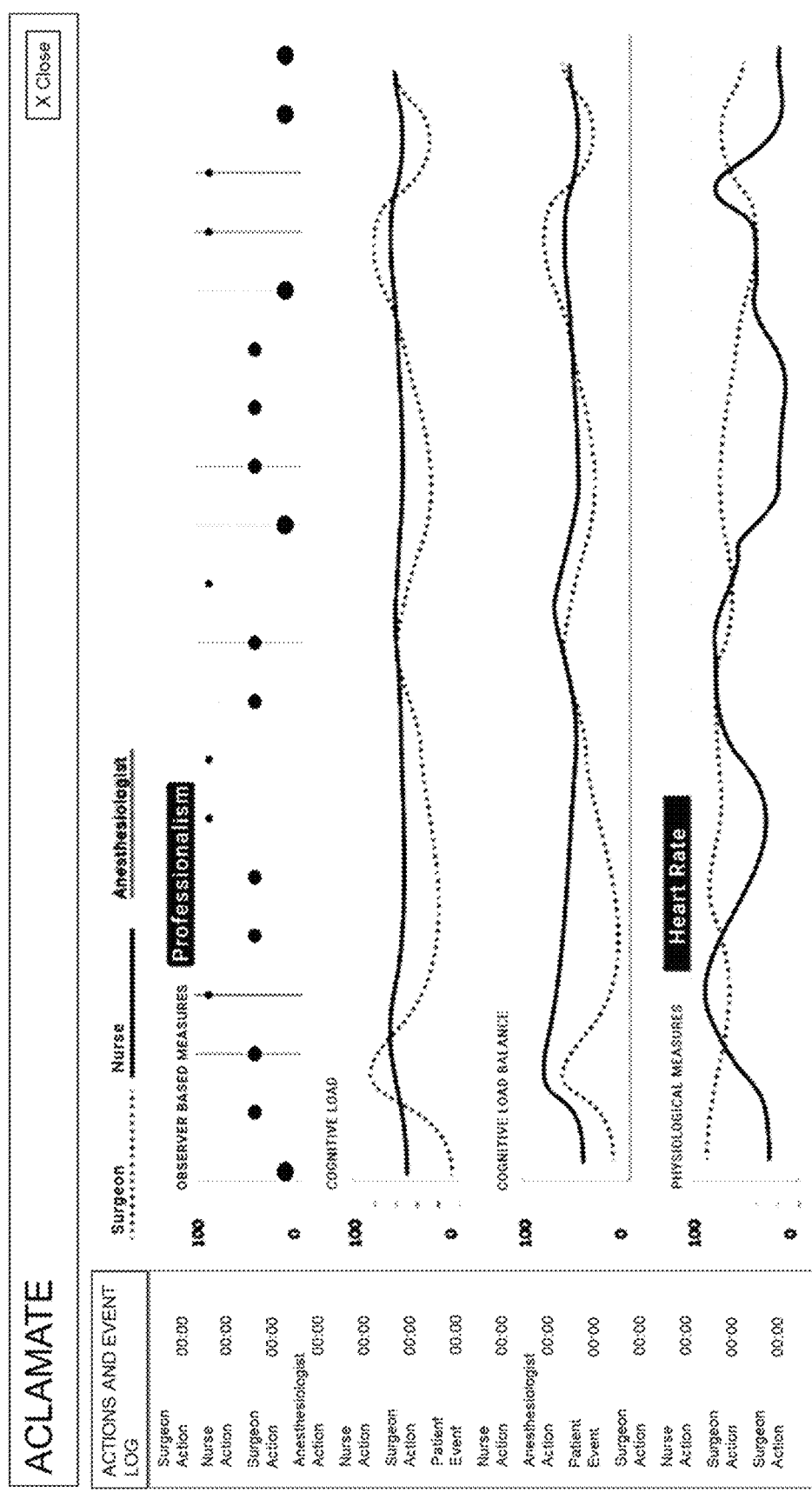
FIG. 4B illustrates an example embodiment of a user interface showing a "detailed view" dashboard.

FIG. 4B includes the dashboard design constructed for a detailed view real-time visualization. This provides a "deep-dive" for system users to look at system measures and metrics collected over time during a simulation scenario. This view allows an instructor and simulation specialist to review current and historical trends in important system-generated measures.

Figure 4C:
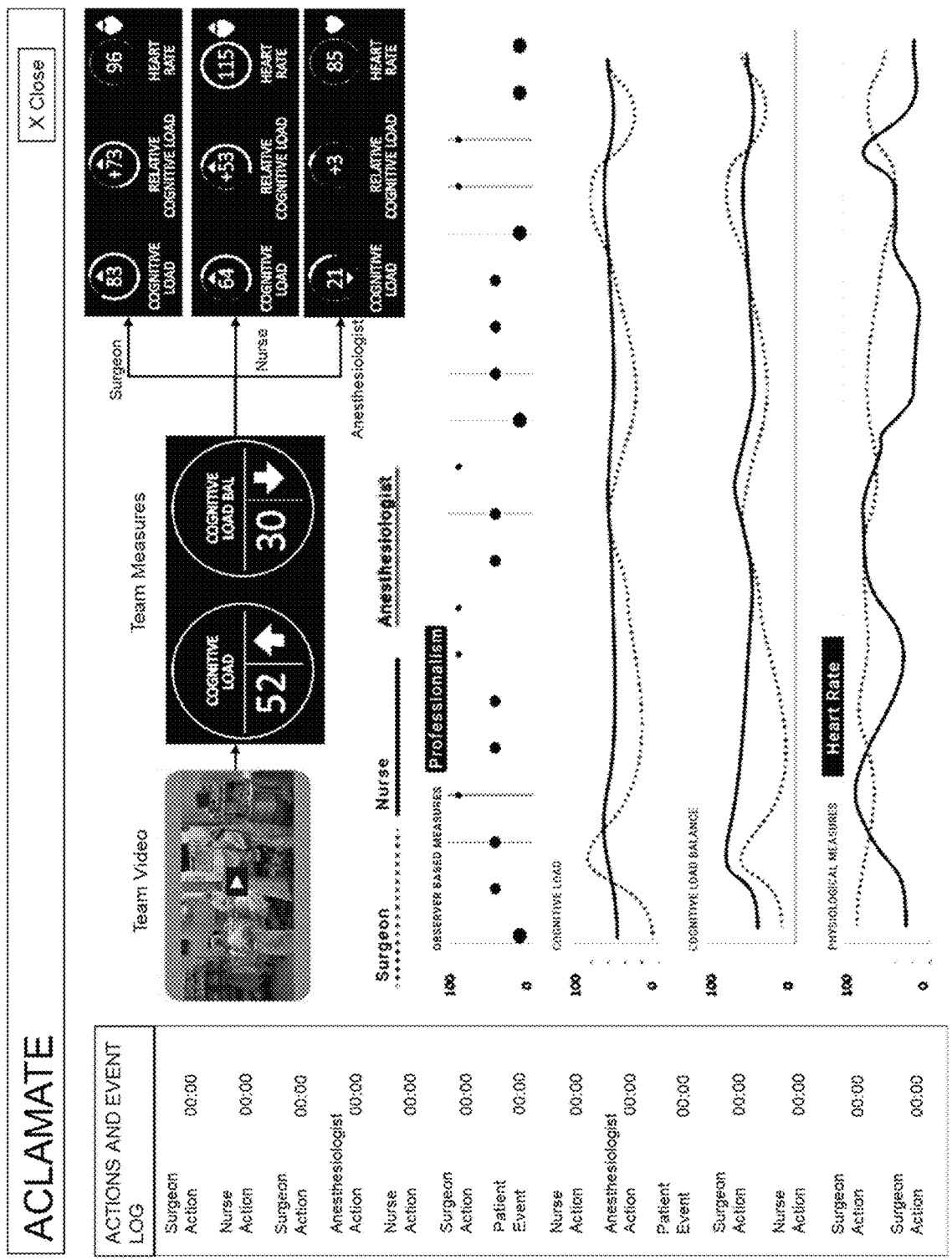
FIG. 4C illustrates an example embodiment of a user interface showing a "after action report" dashboard.

FIG. 4C includes an example dashboard design for an AAR module detailed view with video playback capabilities embedded within it. The video of the setting may be made with an IP camera. This dashboard design draws from all of the design elements of the detailed view and provides data tracking and playback capabilities for all data sources and measures generated by the system during a simulation session. These data sources include: relevant physiological features (e.g. heart rate, features from EEG power spectrum), individual/team-level cognitive load measures, occurrence significant events\actions occurring during a scenario, video of the event with event\action time-stamps referenced to key points in time within video, and observer ratings of individual and team performance. Displayed on the screen is a measure of individual and team workload assessments. The display may also show a vertical bar to indicate what point in time the user is focusing on. As shown, the interface may also have a recording of the team's actual performance and a real-time assessment of team workload. Along the left hand side of the screen is an actions and events log showing cognitive load indicators for that actions and/or event.

Although not shown in FIG. 4, the display may also have markers that represent instructor ratings of team or individual performance. The markers may be color coded to represent the different skills that were assessed by the observer (e.g., blue=decision making, gray=situation awareness). Each marker can appear on the workload graph at the appropriate time stamp. Each marker may also include a modifier (white up arrow or down arrow) to indicate whether the rating indicated effective or ineffective performance. Some embodiments may further have a time-stamped list of all the observer-based ratings that may be sortable and filterable. Further, the display may also show horizontal bars which indicate average workload (green) vs. statistically significantly boundaries of high and low (both indicated in red) workload.

Figure 5:
FIG. 5 illustrates an example embodiment of a user interface showing a "after action report" dashboard emphasizing video and event/action visualization.

FIG. 5 includes the dashboard design for the AAR module with a view which provides emphasis on video playback and events/actions occurring on the screen. Unlike FIG. 4, this dashboard visualization does not provide time series plots of the various system-generated data sources listed above. This visualization is accessible from the AAR detailed view and focuses on the presentation of video and key events/actions recorded by the Android application during a scenario. This view can be easily toggled from the AAR detailed view dashboard.

The data shown through the user interface may be time synchronized. Therefore, it will be possible to scroll through one data element and have the results propagate throughout the other elements (across both displays). For example, clicking on an item from the surgical checklist (left side of left hand screen) will scroll the high-definition video to the appropriate point in time; it will also scroll the vertical indicator bar on the workload display to identify the level of team workload at that time. By linking all of the data using a common time stamp, the trainer will be able to facilitate an accurate and efficient AAR. Should the trainer wish to focus the discussion on team workload, for example, he or she can immediately scroll to those time segments where workload was significantly elevated (or lower); the trainer can then work with the team to discuss what was occurring at that specific time by leveraging contextual information from the surgical checklist, the video, and the observer-based ratings. Alternatively, if the trainer wanted to focus the discussion on the observer-based ratings (such as the Accreditation Council for Graduate Medical Education (ACGME) competencies), he or she could select ratings that were particularly low (or high) and then explore the reasons why by leveraging contextual information from the workload display, surgical checklist, and high-definition video. The critical point is that this display provides the trainer with maximum flexibility for determining how to structure and conduct the AAR. In some embodiment, additional drill-down functionality is provided to allow the users to analyze system data in more detail.

In some embodiments, the user interface is configured to communicate the CL measures at two points in time: during the scenario (real-time display available to the instructor only), and during the AAR (retrospective playback available to all team members, including the instructor). Communicating measures at these times is helpful to accommodate learning during the post-training AAR. During this time, team members are provided with the time to systematically reflect on what they did well, what they did poorly, and what they need to do differently moving forward. Therefore, it has been found helpful to incorporate the unobtrusive measures into AARs to help diagnose the causes of particularly effective or ineffective performance.

In some embodiments, the different data streams are time-synchronized and the user interface is configured so that an instructor can navigate, sort, or filter the data in multiple ways. Instructors generally like the freedom to change their methods, as necessary, to suit the situation. For example, an instructor might normally lead a post-training AAR based on which competencies the team did particularly well (or poorly) on. Alternatively, the instructor might want to step through each phase of the scenario in chronological order.

In some embodiments, the user interface is configured to present the measures in such a way that they can be readily interpreted, such as on a 100-point scale or using color codes (e.g., red, yellow, green) to identify different levels of functioning. While many users may have medical degrees, they may be unfamiliar with how EEG, ECG, GSR, and related sensor information could be used to infer group-level characteristics such as team workload, stress, or task engagement.

In some embodiments, the user interface may have a "control panel" which allows instructors to dynamically enable (or disable) various display elements, as necessary, to ensure the most effective AAR possible.

Testing Results of One Example Embodiment of the ACLAMATE System

Figure 6:
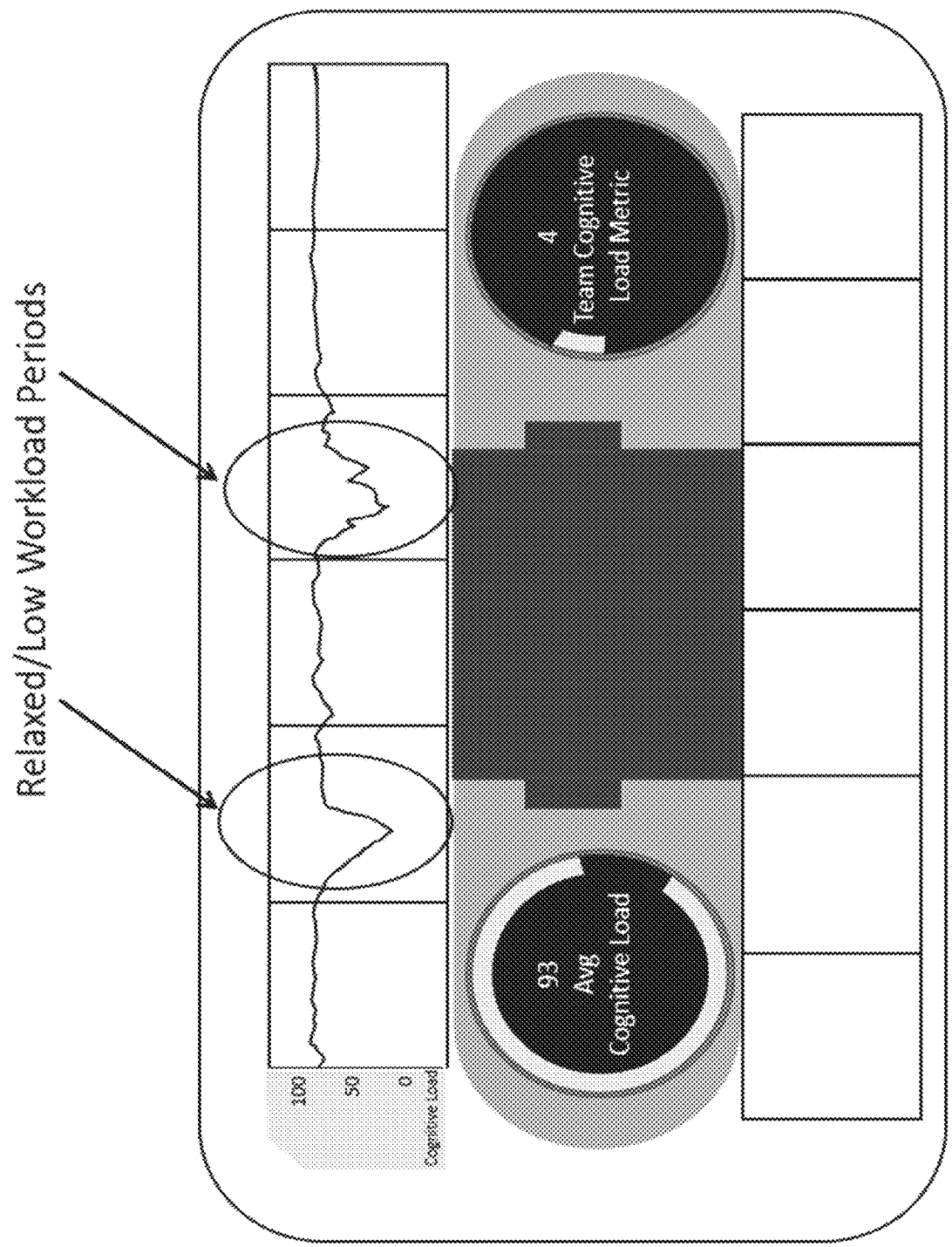
FIG. 6 illustrates an example embodiment of a user interface reflecting actual pilot testing.

For pilot testing of one example embodiment of a simulation based training system with cognitive load assessment subsytems, two individuals tested the functionality of a simulation based training system in a simulated operating room that contains multiple wireless patient monitoring technologies. The wireless neurophysiological monitors and EEG caps (placed underneath the surgical caps) were connected to each participant. During the pilot test, the two individuals performed a series of activities that were designed to elicit different levels of RCL and CLB, and we were able to verify that the real-time measures were responsive to the task demands. For example, there were two time periods (at approximately 3 minutes and again at 9 minutes into the test procedure, respectively) where the participants were specifically asked to relax. These regions of low workload are easily identified on the visualization (see FIG. 6).

Three clinically relevant example scenarios were developed. The three scenarios consist of patient care crises including: loss of airway, venous air embolism, and hemorrhage. These scenarios have been designed with a series of "transition cues" that are intended to induce significant changes in team CL. These scenarios can be easily modified and reprogrammed to increase difficulty, and consequently allow us to measure changes in workload across members of a healthcare team, as well as across time. These "transition cues" can consist of factors such as changes in team composition (e.g., a senior member of the team being called away to treat another patient), or instituting multiple clinical complications in the patient manikin's condition (e.g., due to changes in fluids, anesthesia/analgesics/anaphylaxis, ionotropy, sepsis, surgical compression, oxygenation, temperature, pneumothorax, embolism, drugs, glucose levels, and the like).

Cognitive load models were developed to utilize features derived through signal processing and feature extraction algorithms developed. All raw electrocardiogram (ECG) and electroencephalogram (EEG) data collected by the system were subjected to artifact correction, de-noising, and signal processing algorithms to "clean" the data of motion artifacts induced during mobile healthcare environments. Input features (derived on a second by second basis) utilized by the cognitive load models included: average interbeat interval (IBI), filtered heart rate, percentage heart rate deviation from baseline heart rate estimate, and absolute power values derived from the EEG power spectrum at electrode sites Fz, Pz, and O2.

Figure 8:
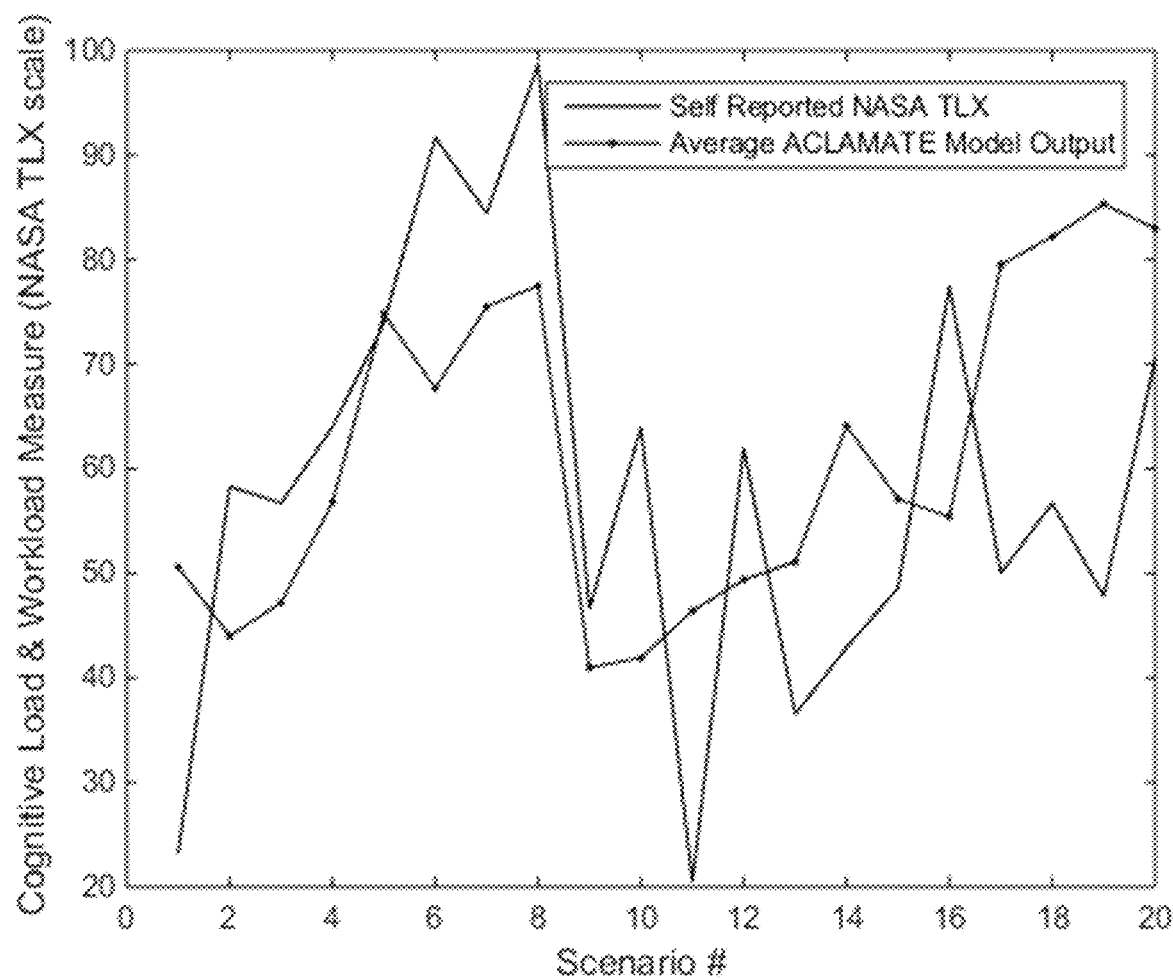
FIG. 8 illustrates a comparison of self-reported NASA TLX ratings versus average cognitive load output from the ACLAMATE model across 20 scenarios (training content)

A total of 5 cognitive load models were built using the features and data described above. The data from a single subject was randomly excluded from the model training set in order to validate model performance in a real-world setting. The developed models accurately tracked trends in cognitive load across the five subjects utilized for model validation. Additionally, the absolute difference between the average cognitive load model output with respect to self-reported NASA TLX collected at the conclusion of each simulation scenario was 17.54 across 20 scenarios. The correlation of average cognitive load model output with respect to NASA TLX values was calculated as 0.35. While this result indicates there is a positive correlation between average model output and self-reported values, the correlation value is not higher due to the fact that each scenario consisted of "lull periods" where cognitive load was not stimulated significantly. In this regard, it is more beneficial for the models to track changes in cognitive load on a second by second basis rather than overall as an average measure. Second by second cognitive load model classification accuracy was calculated as 78.1% overall. FIG. 8 demonstrates average cognitive model output per scenario versus NASA TLX (self-reported cognitive load\workload). As shown, the developed model effectively tracks trends in self-reported workload across each of the five subjects.

Alternative Embodiments of Simulation Based Training Systems for Measurement of Cognitive Load to Customize Simulation Content The simulation based training system interfaces may further include the ability to configure the system to create custom studies and/or simulation sessions for use by simulation centers and facilities. Additionally, the cognitive load assessment system may allow users to define the number of study participants, their roles, and the various physiological sensors and data sources being used to monitor each participant.

The simulation based training system may further include a user interface application, such as an Android or other table or phone application, for use with the system which acts as a video capturing tool and an event/action logger. The application may control an IP camera over a local Wi-Fi network and logs events and actions for future use by the system's after action review (AAR) module. This application allows users to log actions made by participants being monitored as either good/desirable or bad/inappropriate. Additionally, this tool may allow users to log significant events occurring during a simulation scenario and patient status events which correspond to different segments or time periods of a scenario. The patient status events may be categorized as three potential states: (1) moderate patient status change, (2) serious patient status change, and (3) life-threatening patient status change.

The simulation based training system may also include alerts to indicate when disconnections occur between the system components and the physiological monitors. The simulation based training system software charged with processing and visualization of real-time physiological data may contain a status indicator as well as an overall signal quality metric to indicate the overall percentage of data received during a data collection session.

The simulation based training system may include new emerging technologies as sensors. For example, functional near infrared imaging (fNIR) as well as more low cost and non-invasive sensor technologies such as the Zephyr Bio-Harness may be used to measure variables such as heart rate, respiration rate, galvanic skin response, and other autonomic bodily responses.

Figure 10:
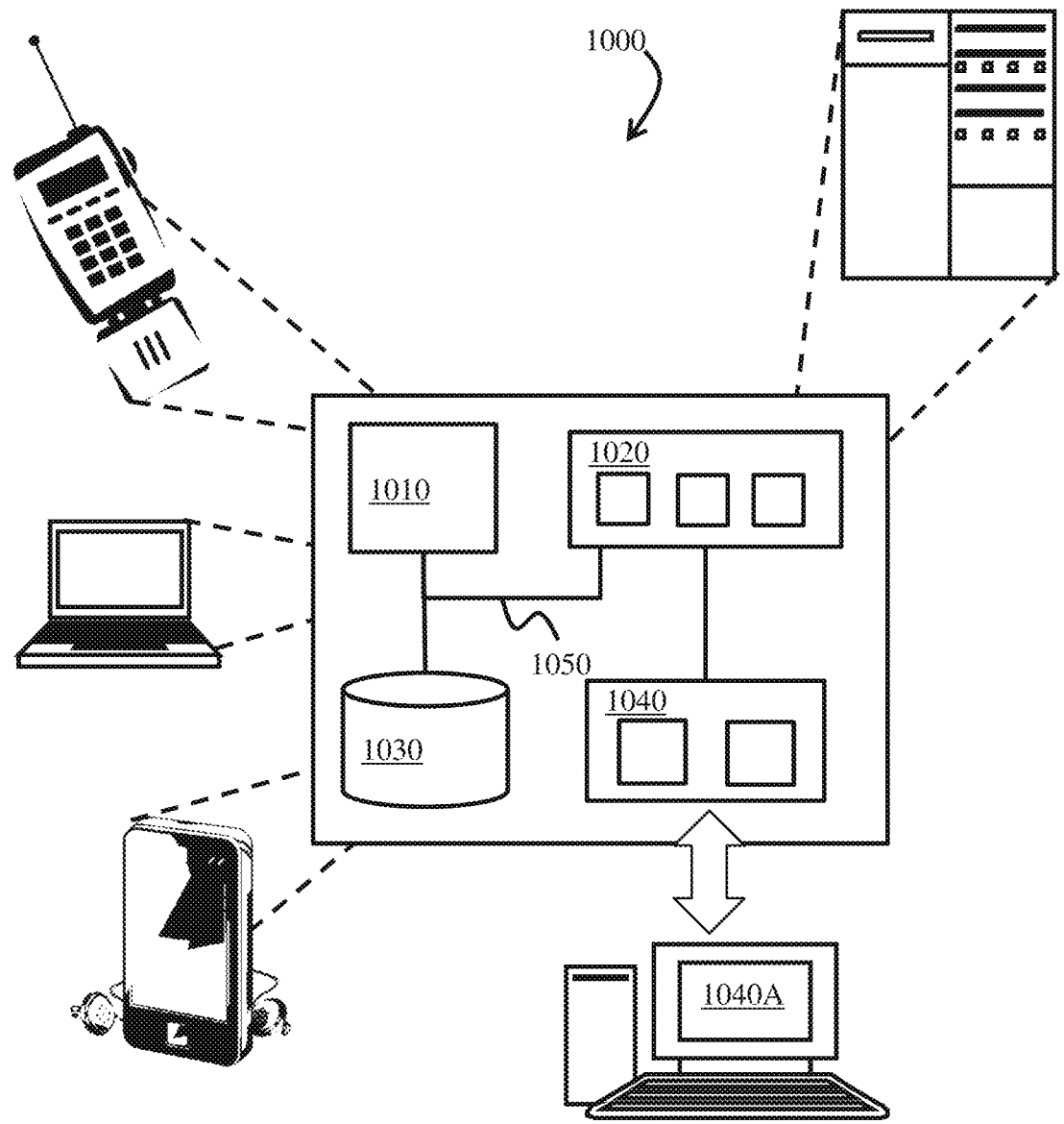
FIG. 10 illustrates one example embodiment of a computer system suitable for a cognitive load assessment subsystem or simulation based training system.

Embodiments of the Simulation Based Training Systems for Measurement of Cognitive Load to Customize Simulation Content Implemented with Software One embodiment of the simulation based training system may comprise some of the functional elements of FIGS. 1A, 1B and 3 implemented in a software program product to be executed by a computer implemented system such as the example embodiment illustrated in FIG. 10.

As will be readily apparent to those skilled in the art, portions of the simulation based training systems and methods can be embodied in hardware, software, or a combination of hardware and software. For example, a computer system or server system, or other computer implemented apparatus combining hardware and software specifically adapted for carrying out the methods described herein, may be suitable. One embodiment of a combination of hardware and software could be a general purpose computer system with a computer program that, when loaded and executed, carries out the respective methods described herein. In some embodiments, a specific use computer, containing specialized hardware for carrying out one or more of the instructions of the computer program, may be utilized. In some embodiments, the computer system may comprise a device such as, but not limited to a digital phone, cellular phone, laptop computer, desktop computer, digital assistant, server or server/client system.

Computer program, software program, program, software or program code in the present context mean any expression, in any language, code or notation, of a set of instructions readable by a processor or computer system, intended to cause a system having an information processing capability to perform a particular function or bring about a certain result either directly or after either or both of the following: (a) conversion to another language, code or notation; and (b) reproduction in a different material form. A computer program can be written in any form of programming language, including compiled or interpreted languages, and it can be deployed in any form, including as a stand-alone program or as a module, component, subroutine, or other unit suitable for use in a computing environment.

FIG. 10 is a schematic diagram of one embodiment of a computer system 1000 by which the environmental system reaction methods may be carried out. The computer system 1000 can be used for the operations described in association with any of the computer implemented methods described herein. The computer system 1000 includes at least one processor 1010, a memory 1020 and an input/output device 1040. Each of the components 1010, 1020, and 1040 are operably coupled or interconnected using a system bus 1050. The computer system 1000 may further comprise a storage device 1030 operably coupled or interconnected with the system bus 1050.

The processor 1010 is capable of receiving the instructions and/or data and processing the instructions of a computer program for execution within the computer system 1000. In some embodiments, the processor 1010 is a single-threaded processor. In some embodiments, the processor 1010 is a multi-threaded processor. The processor 1010 is capable of processing instructions of a computer stored in the memory 1020 or on the storage device 1030 to communicate information to the input/output device 1040. Suitable processors for the execution of the computer program instruction include, by way of example, both general and special purpose microprocessors, and a sole processor or one of multiple processors of any kind of computer.

The memory 1020 stores information within the computer system 1000. Memory 1020 may comprise a magnetic disk such as an internal hard disk or removable disk; a magneto-optical disk; an optical disk; or a semiconductor memory device such as PROM, EPROM, EEPROM or a flash memory device. In some embodiments, the memory 1020 comprises a transitory or non-transitory computer readable medium. In some embodiments, the memory 1020 is a volatile memory unit. In another embodiment, the memory 1020 is a non-volatile memory unit.

The processor 1010 and the memory 1020 can be supplemented by, or incorporated in, ASICs (application-specific integrated circuits).

The storage device 1030 may be capable of providing mass storage for the system 1000. In various embodiments, the storage device 1030 may be, for example only and not for limitation, a computer readable medium such as a floppy disk, a hard disk, an optical disk, a tape device, CD-ROM and DVD-ROM disks, alone or with a device to read the computer readable medium, or any other means known to the skilled artisan for providing the computer program to the computer system for execution thereby. In some embodiments, the storage device 1030 comprises a transitory or non-transitory computer readable medium.

In some embodiments, the memory 1020 and/or the storage device 1030 may be located on a remote system such as a server system, coupled to the processor 1010 via a network interface, such as an Ethernet interface.

The input/output device 1040 provides input/output operations for the system 1000 and may be in communication with a user interface 1040A as shown. In one embodiment, the input/output device 1040 includes a keyboard and/or pointing device. In some embodiments, the input/output device 1040 includes a display unit for displaying graphical user interfaces or the input/output device 1040 may comprise a touchscreen. In some embodiments, the user interface 1040A comprises devices such as, but not limited to a keyboard, pointing device, display device or a touchscreen that provides a user with the ability to communicate with the input/output device 1040.

The computer system 1000 can be implemented in a computer system that includes a back-end component, such as a data server, or that includes a middleware component, such as an application server or an Internet server, or that includes a front-end component, such as a client computer having a graphical user interface or an Internet browser, or any combination of them. The components of the system can be connected by any form or medium of digital data communication such as a communication network. Examples of communication networks include, e.g., a LAN, a WAN, wireless phone networks and the computers and networks forming the Internet.

A functional diagram of one embodiment of the computer program capable of executing the described methods is shown in FIG. 3.

One example embodiment of the automated cognitive load assessment systems and methods may be embodied in a computer program product, the computer program product comprising a computer readable medium having a computer readable program code tangibly embodied therewith, the computer program code configured to implement the methods described herein, and which, when loaded in a computer system comprising a processor, is able to carry out these methods.

One Embodiment of the Simulation Based Training Systems for Measurement of Cognitive Load to Customize Simulation Content in Operation For purposes of illustrating the operation of one embodiment of a simulation based training system, and not for limitation, the operation of a simulation based training system is summarized in the process diagram of FIG. 3. As shown in FIG. 3, the process may include the monitoring of more than one user. For ease of illustration, the process will be described for one user following the process steps identified with the "A" call-out designation.

The process of operation generally starts with the step of 302 where the simulation content is communicated to the users through the user interface of the simulator.

At 320 the sensors receive signals from the first user and communicates them to the Physique module.

At 330, the first raw data is received in a format compliant with the cognitive load assessment subsystem. For example, the raw data packets are received and transformed into values such as numeric values.

At 342, the $FuSE^2$ module translates data received from the Physique client and determines the cognitive load measures. The "translation" at 335A and 335B includes processing/conversion to aggregate input variables into a common value. For example, to address a situation where a CL model is executed every second, but we get a variable (e.g. HR) 3 times a second, we first configure $FuSE^2$ module to extract that variable out of the data stream and determine how it should aggregate that data into a single input value. In this example, since the model accepts a single value for a given variable, this extraction and aggregation can be to take a simple average of the multiple variable, or take just taking the last known value. This can be done for all inputs required by the cognitive load model(s). This type of translation is significant because all the input data needs to be synced in time and not all input variables come from the same source or at the same rate.

At step 342A, the individual cognitive load is determined by the $FuSE^2$ module using the individual cognitive load models. The cognitive load models use the the extracted and/or translated values from the Physique module as input to the cognitive load algorithms as described herein.

At this point, the individual cognitive load measure may be stored in the database as step 370 or this measure may be compared with another user for the creation of a team cognitive load measure using the team cognitive load model at step 342C.

These cognitive load measures may also be shared with the Cognitive Load Assessment Tool Kit 380 components (e.g., APIs) for further processing. For example, the measures may be communication to a user interface for feedback at step 382; the measures may be added to or compared to a measure database and provided at step 384; or the measures may be used for comparison to a threshold and if the threshold is exceeded and alarm is communicated to a user at step 386.

In some embodiments, the cognitive load measures may be used to customize cognitive load content at 388. Simulation content may be customized by selecting the next simulation content for presentation through the simulator user interface to the user at 302. For example, the next simulation content may be selected by comparing the CL measure to a database of simulation content at 387 to identify which simulation content from the simulation content database 389 would present the most appropriate content to the user. For example, the data in the simulation content database may be formatted in a manner, such as in a table, that allows a mapping of the present CL to a simulation content with an expected resulting CL for the users, and the most appropriate simulation content may be the content that would have the expected resulting CL with the highest probability of keeping the user in the ZPD.

In some embodiments, self-reported measures may be taken as shown in step 350. These self-reported measures may be provided as feedback to a system user interface and they may be stored in the system database at 370.

As shown in FIG. 3, for those process steps that may be repeated with a second or other numbers of users, some of those steps are shown with a "B" call-out designation reflecting the same general process as identified above with the "A" call-out designation.

Although this invention has been described in the above forms with a certain degree of particularity, it is understood that the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention which is defined in the claims and their equivalents.

We claim:

1. A simulation based training system for real-time measurement of a cognitive load of a user to automatically customize a simulation content for the user, the simulation based training system comprising:
   a processor based simulator comprising:
      a user interface,
      a cognitive load measuring subsystem, and
      a simulation content customization subsystem;
   the user interface configured to present a first simulation content to a user;
   a sensor comprising a physiological sensor configured to capture a raw input from the user and communicate the raw input to the cognitive load measuring subsystem;
   the cognitive load measuring subsystem comprising:
      a processor,
      an input translator configured to translate the input to a compliant input value, and
      a predefined individual cognitive load model configured to determine a cognitive load measure from the compliant input value;
   the cognitive load measuring subsystem configured to communicate the user cognitive load measure to the simulation content customization subsystem;
   the simulation content customization subsystem configured to determine a second simulation content based on the based on the cognitive load measure and communicate the second simulation content to the user interface;
   the processor based simulator configured to communicate the second simulation content to the user interface as a customized simulation content;
   the cognitive load measuring subsystem further comprises a predefined range of measures for a Zone of Proximal Development (ZPD) for the user; and
   the simulation content customization subsystem determines the second simulation content based on a comparison of the cognitive load measure to the ranges of measures for the ZPD for the user whereby a second cognitive load measure is more likely to be within range of measures for the ZPD.

2. The simulation based training system of claim 1 wherein the second simulation content comprises a media file.

3. The simulation based training system of claim 1 wherein the predefined individual cognitive load model comprises a time-delay neural network (TDNN).

4. The simulation based training system of claim 1 wherein the first sensor comprises an ECG sensor and the raw input is an ECG data.

5. The simulation based training system of claim 1 wherein the sensor comprises an EEG sensor and the raw input is an EEG data.

6. The simulation based training system of claim 1 wherein the sensor comprises a wireless neurophysiological monitor.

7. The simulation based training system of claim 1 wherein the sensor is a sociometric sensor.

8. The simulation based training system of claim 1 wherein the sensor is an audio sensor.

9. The simulation based training system of claim 1 wherein the sensor is a physiological sensor.

10. A simulation based training system for real-time measurement of a cognitive load of a user to automatically customize a simulation content for the user, the simulation based training system comprising:
   a processor based simulator comprising:
      a user interface,
      a cognitive load measuring subsystem, and
      a simulation content customization subsystem;
   the user interface configured to present a first simulation content to the user;
   a sensor comprising a physiological sensor configured to capture a raw input from the user and communicate the raw input to the cognitive load measuring subsystem;
   the cognitive load measuring subsystem comprising:
      a processor,
      an input translator configured to translate the raw input to a compliant input value, and a predefined individual cognitive load model configured to determine a cognitive load measure from the compliant input value;
   the cognitive load measuring subsystem configured to communicate the cognitive load measure to the simulation content customization subsystem;
   the simulation content customization subsystem configured to determine a second simulation content based on the based on the cognitive load measure and communicate the second simulation content to the user interface;
   the processor based simulator configured to communicate the second simulation content to the user interface as a customized simulation content; and wherein the predefined individual cognitive load model comprises a time-delay neural network (TDNN).

11. The simulation based training system of claim 10 wherein the predefined individual cognitive load model comprises a time-delay neural network (TDNN).

12. The simulation based training system of claim 10 wherein the sensor comprises an EEG sensor and the raw input is an EEG data.

13. The simulation based training system of claim 10 wherein the sensor comprises a wireless neurophysiological monitor.

14. The simulation based training system of claim 10 wherein the sensor is a sociometric sensor.

15. The simulation based training system of claim 10 wherein the sensor is an audio sensor.

16. The simulation based training system of claim 10 further comprising:
   a second sensor comprising a second sensor configured to capture a second raw input from a second user and communicate a second raw input to the cognitive load measuring subsystem;
   a team cognitive load model configured to determine a team cognitive load value from the cognitive load value and a second cognitive load value;
   a relative cognitive load model configured to determine a relative cognitive load value from the team cognitive load value and one or more of the cognitive load value and the second cognitive load value; and
   the simulation content customization subsystem further configured to determine the second simulation content based on the relative cognitive load value.

17. The simulation based training system of claim 16 wherein:
   the cognitive load measuring subsystem further comprises a predefined range of values for a Zone of Proximal Development (ZPD) for the team; and
   the simulation content customization subsystem determines the second simulation content based on a comparison of the cognitive load value to the ZPD for the user whereby a second cognitive load measure is more likely to be within the ZPD.

18. The simulation based training system of claim 10 wherein the sensor is a physiological sensor.

19. A simulation based training system for real-time measurement of a cognitive load of a user to automatically customize a simulation content for the user, the simulation based training system comprising:
   a processor based simulator comprising:
      a user interface,
      a sensor,
      a cognitive load measuring subsystem, and
      a simulation content customization subsystem;
   the user interface configured to present a first simulation content to the user;
   the sensor configured to capture an input from the user to the first simulation content and communicate the input to the cognitive load measuring subsystem;
   the cognitive load measuring subsystem comprising:
      a processor, and
      a cognitive load model configured to determine a cognitive load measure from the input;
   the cognitive load measuring subsystem configured to communicate the cognitive load measure to the simulation content customization subsystem;
   the simulation content customization subsystem configured to determine a second simulation content based on the based on the cognitive load measure and communicate the second simulation content as a second simulation content to the user interface;
   the processor based simulator configured to communicate the second simulation content to the user interface as a customized simulation content;
   the cognitive load measuring subsystem further comprises a predefined range of values for a Zone of Proximal Development (ZPD) for the user; and
   the simulation content customization subsystem determines the second simulation content based on a comparison of the cognitive load value to the ZPD for the user whereby a second cognitive load measure is more likely to be within the ZPD.

20. The simulation based training system of claim 19 wherein the sensor is a physiological sensor.

* * * * *